(12) United States Patent
Marth et al.

(10) Patent No.: US 6,376,475 B1
(45) Date of Patent: Apr. 23, 2002

(54) CONTROL OF IMMUNE RESPONSES BY MODULATING ACTIVITY OF GLYCOSYLTRANSFERASES

(75) Inventors: Jamey D. Marth, San Diego; James C. Paulson, Del Mar, both of CA (US)

(73) Assignee: Abaron Biosciences, Inc., Del Mar, CA (US)

( * ) Notice: Subject to any disclaimer, the term of this patent is extended or adjusted under 35 U.S.C. 154(b) by 0 days.

(21) Appl. No.: 09/087,117

(22) Filed: May 29, 1998

Related U.S. Application Data

(60) Provisional application No. 60/048,303, filed on May 30, 1997.

(51) Int. Cl.[7] .............................. C12Q 1/48; C12N 9/10; C12N 5/08; A61R 31/7064; A61K 45/00

(52) U.S. Cl. ..................... 514/49; 435/193; 435/372.2; 435/372.3; 435/15; 514/789

(58) Field of Search ................ 514/789, 79; 435/372.3, 435/372.2, 15, 193

(56) References Cited

U.S. PATENT DOCUMENTS

| | | | |
|---|---|---|---|
| 5,288,854 A | * 2/1994 | Diamond et al. | 530/395 |
| 5,352,462 A | * 10/1994 | Beck | 424/278.1 |
| 5,441,932 A | 8/1995 | Kodama et al. | 514/8 |
| 5,453,272 A | 9/1995 | Heerze et al. | 424/190.1 |
| 5,461,143 A | * 10/1995 | Wong et al. | 536/17.5 |

FOREIGN PATENT DOCUMENTS

| | | |
|---|---|---|
| WO | WO 95/34202 | 12/1995 |

OTHER PUBLICATIONS

Lo et al. Biochemical and Biophysical Research Communications 228:380–385 (1996).*

Kleineidam et al. "Studies on the inhibition of sialyl– and galactosyltransferases" (1997) Glycoconjugate Journal 14:57–66.*

Braesch–Abderson et al. *J. Biol. Chem.* (Apr. 1994) 269: 11783–11786.

Hanasaki et al. *J. Biol. Chem.* (Apr. 1994) 269(14): 10628–10636.

Hennett et al. *Proc. Natl. Acad. Sci. USA* (Apr. 1998) 95: 4504–4509.

Powell et al. *J. Biol. Chem.* (Apr. 1993) 268: 7019–7027.

Powell et al. *J. Biol. Chem.* (Apr. 1994) 269: 10628–10636.

Sgroi et al. *J. Biol. Chem.* (Apr. 1993) 268: 7011–7018.

Stamenkovic et al. *Cell* (Sep. 20, 1991) 66: 1133–1144.

J.C. Paulson et al. *J. Biol. Chem.* (Aug. 25, 1978) 253(18):5617–5624.

C. Schaub et al. *Glycoconjugate Journal* (1998) 15: 345–354.

P. Maly et al. *Cell* (1996) 86: 643–653.

* cited by examiner

*Primary Examiner*—Rebecca E. Prouty
*Assistant Examiner*—David J. Steadman
(74) *Attorney, Agent, or Firm*—Townsend & Townsend & Crew LLP

(57) ABSTRACT

The invention provides methods for inhibiting immune responses by inhibiting the biosynthesis of the sialyl galactosides that are involved in immune responses. In particular, B lymphocyte-mediated immune responses are mediated by interfering with synthesis of α2,6 sialylgalactosides, while T lymphocyte-mediated immune responses are inhibited by blocking synthesis of α2,3 sialylgalactosides. The inhibition is accomplished by, for example, inhibiting the activity of a glycosyltransferase involved in synthesis of the respective sialyl galactoside.

19 Claims, 6 Drawing Sheets

CONTROL OF IMMUNE RESPONSES BY MODULATING ACTIVITY OF GLYCOSYLTRANSFERASES

CROSS-REFERENCE TO RELATED APPLICATIONS

This application claims benefit of U.S. provisional application Ser. No. 60/048,303, filed May 30, 1997, which application is incorporated herein by reference for all purposes.

BACKGROUND OF THE INVENTION

1. Field of the Invention

The present invention relates to the field of modulating immune responses by administering an agent that influences the structure of sialyl galactosides that are present on cells involved in immune responses.

2. Background

While all eukaryotic cell surfaces are covered by oligosaccharides, vertebrate cells specifically display a more diverse and complex repertoire in part by the production of unique asparagine-linked oligosaccharide structures (Kornfeld and Kornfeld, *Ann. Rev. Biochem.*, 54:631 (1985); Varki and Freeze, In: *Subcellular Biochemistry: Membrane Biogenesis,* (eds, Maddy and Harris, Plenum Press, New York), v.22, pp.71 (1994)). The vertebrate glycosyltransferase gene superfamily controls the biosynthesis and diversification of cell surface oligosaccharides (Schachter, *Curr. Opin. Struct. Biol.*, 1, (1991); Kleene and Berger, *Biochim. Biophys. Acta,* 1154:283 (1993); Marth, *Glycoconjugate J.* 11, 3 (1994)). These Type II transmembrane enzymes harbor exquisite substrate specificities and are organized in the Golgi apparatus to function in the stepwise production of oligosaccharides. Oligosaccharide diversification in phylogeny, ontogeny, cell activation and tumorigenesis is due to organism- and cell type-specific glycosyltransferase gene expression profiles (Varki and J. D. Marth, in: *Seminars in Developmental Biology* 6:127 (1995)).

Intercellular recognition and adhesion is a complex phenomenon responsible for numerous cellular interactions, such as fertilization, cell migration, organ formation, and immune defense. The high selectivity required by these processes is often provided by lectins, a class of nonimmunogenic proteins that bind carbohydrates selectively and noncovalently. Typically, lectins recognize and bind carbohydrates associated with proteins and lipids on the cell surface of the apposing cell. For instance, the CD22 lectin a transmembrane glycoprotein found exclusively on B lymphocytes and is known to play a role in the immunologic activation of these cells (Campana et al. (1985) *J. Immunol.* 134: 1524–1530; Stamenkovic & Seed (1990) *Nature* 345: 74–77; Dorken et al. (1989) in *Leucocyte Typing IV: White Cell Differentiation Antigens,* eds. Knapp et al. (Oxford Univ. Press, Oxford), pp. 63–64). CD 22 has been found associated with the antigen receptor and is a target for tyrosine kinase phosphorylation on the cytoplasmic domain, which thereby recruits various signal transduction molecules (Schulte et al. (1992) *Science* 258: 1001–1004; Leprince et al. (1993) *Proc. Nat'l. Acad Sci. USA* 90: 3236–3240). The extracellular domain of CD22 specifically binds the Sia6LacNAc trisaccharide (Powell et al. (1993) *J. Biol. Chem.* 268: 7019–7027; Sgroi et al. (1993) *J. Biol. Chem.* 268: 7011–7018; Powell & Varki (1994) *J Biol. Chem.* 269: 10628–10636). This trisaccharide ligand exists on several lymphoid cells. Lymphocyte interactions involving CD22 binding to CD45 have been reported (Stamenkovic et al. (1991) *Cell* 66: 1133–1144). As CD22 itself carries Sia6LacNAc, homotypic binding interactions have been shown to occur and may play a regulatory role in immune function (Braesch-Anderson & Stamenkovic (1994) *J. Biol. Chem.* 269: 11783–11786; Hanasaki et al. (1995) *J. Biol. Chem.* 270: 7533–7542). These results suggest that CD22 and Sia6LacNAc are a letin-ligand pair with the potential to control immune cell surface interactions. However, a relatively simple model for CD22 function has not developed from analyses of CD22 null mice by several laboratories (O'Keefe et al. (1996) *Science* 274: 798–801; Otipoby et al. (1996) *Nature* 384: 634–637; Sato et al. (1996) *Immunity* 5: 551–562; Nitschke et al. (1977) *Curr. Biol.* 7: 133–143). Results obtained have inferred both positive and negative roles for CD22 in B lymphocyte immune function, suggesting that CD22 may modulate threshold signaling responses from the antigen-receptor complex.

Despite progress in the identification of lectins and their carbohydrate ligands, a need exists for the discovery of new compositions and methods for the control of cellular interactions associated with them. Such compositions and methods can be used to modulate a number of processes, such as immune responses. The present invention addresses these and other needs.

SUMMARY OF THE INVENTION

The invention provides methods of inhibiting an immune response in a mammal by administering to the mammal a therapeutically effective amount of an agent which causes a reduction in amounts of a sialylated oligosaccharide present in the mammal. The sialylated oligosaccharides generally have a formula that, at the non-reducing end, terminates with Sia$\alpha$2-6Gal- or Sia$\alpha$2,3Gal-. In preferred embodiments, the sialylated oligosaccharide includes Sia$\alpha$2-6Gal$\beta$1-4GlcNAc or Sia$\alpha$2,3Gal$\beta$1-3GalNAc. To inhibit a B lymphocyte-mediated immune response, an agent is used that reduces the amount of oligosaccharides having Sia$\alpha$2-6Gal-, and T lymphocyte-mediated immune responses are inhibited by administering an agent that reduces the amount of oligosaccharides having Sia$\alpha$2,3Gal-.

In another embodiment, the invention provides methods of detecting immunodeficiency or other immune system disorders in a mammal. These methods involve contacting a sample from the mammal, which samples typically contain lymphoid cells, with a detection agent which specifically binds to a sialylated oligosaccharide. The sialylated oligosaccharides of interest generally include the formula Sia$\alpha$2-6Gal- or Sia$\alpha$2,3Gal-. A substantial absence of binding of the detection agent to the lymphocyte is indicative of immunodeficiency.

The invention also provides methods of detecting immunodeficiency or other immune system disorders in a mammal, by detecting the presence or absence of ST6Gal or ST3Gal I sialyltransferase activity in a sample obtained from the mammal. A substantial absence of ST6Gal or ST3Gal I sialyltransferase activity is indicative of immunodeficiency.

Another embodiment of the invention provides mammalian cells that have a genome which includes an inactivating mutation in a gene that encodes a sialyltransferase. The mutation can be one or more of a deletion, a nonsense mutation, an insertion, and a missense mutation. The inactivating mutation can be present in a coding region or a regulatory region of a gene that, in nonmutated form, encodes a sialyltransferase.

Also provided are chimeric non-human mammals that have cells in which the genomes contain an inactivating mutation in a gene that encodes a sialyltransferase. Included are chimeric mammals in which fewer than all cells have the inactivated gene, as well as transgenic mammals in which all cells include the inactivated gene.

DESCRIPTION OF THE FIGURES

FIG. 2A (left panel) presents an analysis of bone marrow lymphocytes for cell surface expression of IgM, CD24 (HSA), CD43 (S7), and B220 by flow cytometry. No deviations were observed in ST6Gal-deficient mice among the percentages (denoted in parentheses) of pro-B cells (B22$^{lo}$CD43(S7)$^+$, gate a (Hardy et al. (1991) *J. Exp. Med.* 173: 1213–1225)), pre-B cells (B220$^{lo}$HSA$^{hi}$, gate b (Carsetti et al. (1995) *J. Exp. Med.* 181: 2129–2140)), immature B cells (B220$^{lo}$IgM$^{int}$, gates b and c (Carsetti et al., supra.)), transitional B cells (B220$^{lo-hi}$ IgW$^{hi}$, gate d (Carsetti et al., supra.)), and mature B cells (B220$^{hi}$ IgM$^{int}$, gate e, and B220$^{hi}$HSA$^{lo}$, gate f (Carsetti et al., supra.)). Percentages shown are the mean of four different analyses with calculated Student's t test, P>4 for all genotypic comparisons indicating no significant variations. FIG. 2A (right panel) shows that ST6Gal-deficient splenic B cells exhibited reductions in cell surface CD22 and IgM, but not in HSA. Reductions in cell surface IgM levels were found to be at 65±20% of controls (Student's t test; P<0.001) and CD22 levels at 38±9% of controls (P<0.001) as determined by comparisons of peak fluorescence (n=8).

FIG. 2B shows that Sia6LacNAc-deficient splenic B cells expressed normal levels of activation markers (CD44, B7.2, and I-A$^b$) and CD40. Dotted lines represent fluorescence of cells stained using an isotype control antibody (n=8).

FIG. 2C presents measurements of serum Ig levels in 4–6 month old unimmunized littermates of indicated genotypes. The median Ig levels are depicted as horizontal bars. Genotypes of 4–6 month old mice are provided on the x-axis. Points represent measurements from single and distinct animals. Results revealed a 63% reduction (P>0.001) in circulating IgM and no statistically significant reduction in IgA or IgG.

In FIG. 3A, B lymphocytes were isolated and stimulated by LPS or by crosslinking IgM or CD40 in the absence and presence of IL-4. Reduced proliferation of Sia6LacNAc-deficient B cells was observed in all experiments in the absence of IL-4. The addition of IL-4 as indicated rescued the defective proliferative response to IgM and CD40 ligation. Proliferation is shown as triplicate measurements of [$^3$H] thymidine incorporation, indicating the mean and SD. Results shown are representative of three different experiments (P<0.005 for IgM crosslinking, P<0.025 for CD40 crosslinking, and P<0.001 for LPS stimulation. FIG. 3B shows an analysis of Ca$^{2+}$ mobilization of B lymphocytes in response to IgM crosslinking (arrow). Sia6LacNAc-deficient B cells exhibited a reduction in amount of cytosolic Ca$^{2+}$ mobilization (63±4% of control value, P<0.01, n=4). FIG. 3C shows that phosphotyrosine accumulation following IgM crosslinking is altered in Sia6LacNAc-deficient B lymphocytes. Splenic B lymphocytes were isolated and stimulated with anti-IgM antibody. At indicated times, cells were lysed and extracts were subsequently analyzed by SDS/PAGE and immunoblotting with anti-phosphotyrosine antibody (n=6). Positions of proteins exhibiting continuously altered levels of phosphotyrosine are denoted by asterisks.

FIG. 4A shows results obtained when T-independent antigen immunization (10 μg of DNP-Ficoll) was followed by analysis of anti-DNP antibody levels in sera at indicated times. FIG. 4B shows results obtained upon T-dependent antigen (DNP-KLH) immunization (10 μg and 100 μg). Anti-DNP antibody levels were measured before and subsequent to a second boost immunization (arrow). Multiple dilutions of sera were assayed to find the linear range of response by OD$_{405}$ measurements. Sera dilution factors for results depicted are as follows: IgM (1/200), IgG$_1$ against T-independent antigen (1/200), IgG$_3$ against T-independent antigen (1/800), IgG$_1$ against T-dependent antigen (1/1,000), and IgG$_3$ against T-dependent antigen (1/200). Data are presented as the mean±SEM from three mice of the indicated genotypes. Use of 0.1 μg of DNA-Ficoll in immunizations resulted in the absence of anti-DNA antibody production specifically in ST6Gal deficient mice, whereas low levels of anti-DNA antibodies were observed in wild-type mice.

FIG. 5A shows the structure of the wild-type mouse ST3Gal I gene as found on genomic clone 129 Sv/J, and the pflox construct that was used to make a targeting vector as shown in FIG. 5B. Upon homologous recombination with the ST3Gal I$^{wt}$ locus in mouse ES cells, as shown in FIG. 5B, ES cells heterozygous for the ST3Gal I$^{F[tkneo]}$ construct were obtained. Cre-mediated recombination with ganciclovir selection resulted in two types of deletions as shown in FIG. 5C, the ST3Gal I$^-$ deletion, which resulted from a Type 1 deletion lacks exon 2 of the ST3 Gal I gene, and the ST3 Gal I$^F$ construct which resulted from a Type 2 deletion.

DESCRIPTION OF THE PREFERRED EMBODIMENTS

Definitions

Figure 1:
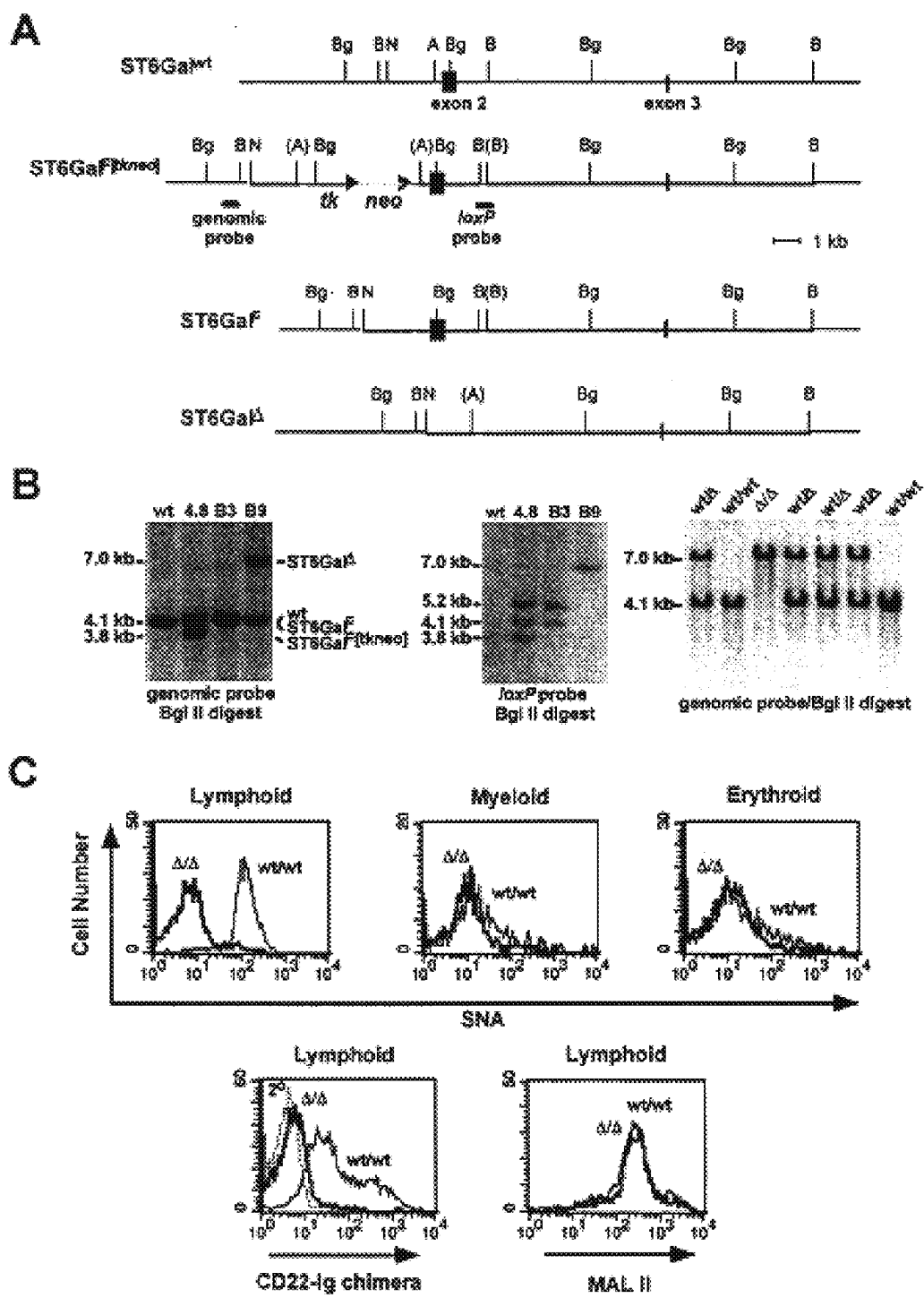
FIG. 1A is a schematic diagram of the ST6Gal genomic structure and the construction of ST6Gal mutants. A partial ST6Gal genomic structure (ST6Gal$^{wt}$) was cloned and used with pflox in constructing a targeting vector (bold line) shown recombined at the ST6Gal locus (ST6Gal$^{F[tkneo]}$) locus in ES cell clone 4.8). Following Cre recombinase expression and ganciclovir selection, ES cell subclones B3 and B9, bearing the ST6Gal$^F$ and the ST6Gal$^\Delta$ allele, respectively, were isolated and used in generating chimeric mice.
FIG. 1B shows genomic Southern blots of ST6Gal alleleic structure in wild-type (wt) ES cells, targeted ES cell clone 4.8 (ST6Gal$^{F[tkneo]}$), 4.8 ES cell subclone B3 (ST6Gal$^F$), and 4.8 ES cell subclone B9 (ST6Gal$^\Delta$) using either a genomic probe outside the targeting vector (left) or a loxP probe (center). At right is shown a genomic Southern blot analysis of offspring derived from matings of mice heterozygous for the ST6Gal$^\Delta$ allele. Genotypes include the presence of mice homozygous for the exon 2 deletion (ST6Gal$^\Delta$).
FIG. 1C presents fluorescent activated cell sorting (FACS) analyses using SNA and CD22-Ig lectins which shows that splenic CD3$^+$ and B220$^+$ lymphocytes specifically express high levels of Sia6LacNAc in comparison with GR-1$^+$ myeloid and Ter-119$^+$ erythroid cells. Lymphocytes from mice homozygous for the B9-derived ST6Gal$^\Delta$ allele were deficient in Sia6LacNAc (n=7). α2,3-linked sialic acids were detected using the MAL II lectin and were found to be expressed at low levels normally and unaltered among cells from mice homozygous for the ST6Gal$^\Delta$ allele (n=7). Mice homozygous for the B3-derived ST6Gal$^F$ allele displayed wild-type profiles in these lectin-based analyses. Similar results were obtained with mesenteric lymph node-derived lymphocytes. Fluorescence signal intensity using an anti-human IgG-FITC conjugate is shown (2° and dotted line, lower left).

The following abbreviations are used herein:

| | |
|---|---|
| Ara = | arabinosyl; |
| Fru = | fructosyl; |
| Fuc = | fucosyl; |
| Gal = | galactosyl; |
| GalNAc = | N-acetylgalacto; |
| Glc = | glucosyl; |
| GlcNAc = | N-acetylgluco; |
| Man = | mannosyl; and |
| NeuAc = | sialyl (N-acetylneuraminyl). |

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

All oligosaccharides described herein are described with the name or abbreviation for the non-reducing saccharide (e.g., Gal), followed by the configuration of the glycosidic bond ($\alpha$ or $\beta$), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2,3). Each saccharide is a pyranose.

Much of the nomenclature and general laboratory procedures required in this application can be found in Sambrook, et al., *Molecular Cloning: A Laboratory Manual* (2nd Ed.), Vol. 1–3, Cold Spring Harbor Laboratory, Cold Spring Harbor, N.Y., 1989. The manual is hereinafter referred to as "Sambrook et al."

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof.

An "inhibitory nucleic acid" is any nucleic acid or modified nucleic acid used or designed for use in inhibitory nucleic acid therapy. "Inhibitory nucleic acid therapy" refers to the use of inhibitory nucleic acids to inhibit gene expression, for example, inhibition of DNA transcription, inhibition of RNA processing, transport or translation, or inhibition of protein synthesis. Inhibitory nucleic acid therapy includes the variety of approaches for treatment of disease using nucleic acids or modified nucleic acids as described herein. Various inhibitory nucleic acid therapies are discussed in detail below.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "heterologous sequence" or a "heterologous nucleic acid", as used herein, is one that originates from a source foreign to the particular host cell, or, if from the same source, is modified from its original form.

A "subsequence" refers to a sequence of nucleic acids or amino acids that comprise a part of a longer sequence of nucleic acids or amino acids (e.g., polypeptide) respectively.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

The term "isolated" is meant to refer to material which is substantially or essentially free from components which normally accompany the enzyme as found in its native state. Thus, the enzymes of the invention do not include materials normally associated with their in situ environment. Typically, isolated proteins of the invention are at least about 80% pure, usually at least about 90%, and preferably at least about 95% pure as measured by band intensity on a silver stained gel or other method for determining purity. Protein purity or homogeneity can be indicated by a number of means well known in the art, such as polyacrylamide gel electrophoresis of a protein sample, followed by visualization upon staining. For certain purposes high resolution will be needed and HPLC or a similar means for purification utilized.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 70%, preferably 80%, most preferably 90–95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when; the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both stands. For amino acid sequences, the BLASTP program uses as defaults a wordlength (W) of 3, an expectation (E) of 10, and the BLOSUM62 scoring matrix (see Henikoff & Henikoff, *Proc. Natl. Acad Sci. USA* 89:10915 (1989)).

In addition to calculating percent sequence identity, the BLAST algorithm also performs a statistical analysis of the similarity between two sequences (see, e.g., Karlin & Altschul, *Proc. Nat.'l Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

"Bind(s) substantially", in the context of nucleic acids, refers to complementary hybridization between a probe nucleic acid and a target nucleic acid and embraces minor mismatches that can be accommodated by reducing the stringency of the hybridization media to achieve the desired detection of the target polynucleotide sequence.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA. The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 50° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium (as the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual,* Cold Spring Harbor Publications, New York, for a description of immunoassay formats and conditions that can be used to determine specific immunoreactivity.

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups each contain amino acids that are conservative substitutions for one another:

1) Alanine (A), Serine (S), Threonine (T);

2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V); and

6) Phenylalanine (F), Tyrosine (Y), Tryptophan (W).

See also, Creighton (1984) *Proteins,* W. H. Freeman and Company. In addition, individual substitutions, deletions or additions which alter, add or delete a single amino acid or a small percentage of amino acids in an encoded sequence are also "conservatively modified variations".

The term "sialic acid" refers to any member of a family of nine-carbon carboxylated sugars. The most common member of the sialic acid family is N-acetyl-neuraminic acid (2-keto-5-acetamindo-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550–11557; Kanamori et al. (1990) *J. Biol. Chem.* 265: 21811–21819. Also included are 9-substituted sialic acids such as a 9-O-C1-C6 acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki (1992) *Glycobiology* 2: 2540; *Sialic Acids: Chemistry, Metabolism and Function,* R. Schauer, Ed. (Springer-Verlag, New York (1992). The synthesis and use of sialic acid compounds in a sialylation procedure is disclosed in international application WO 92/16640, published Oct. 1, 1992.

The term "transgenic" refers to a cell that includes a specific genetic modification that was introduced into the cell, or an ancestor of the cell. Such modifications can include one or more point mutations, deletions, insertions, or combinations thereof. When referring to an animal, the term "transgenic" means that the animal includes cells that are transgenic, and descendants of such animals. An animal that is composed of both transgenic and non-transgenic cells is referred to herein as a "chimeric" animal.

DETAILED DESCRIPTION

The present invention provides compositions and methods for inhibiting immune responses that are mediated in part by 2,6-sialylgalactosides and 2,3-sialylgalactosides. These sialylgalactosides are ligands for cell surface molecules involved in intercellular adhesion and signal transduction, such as, for example, CD22. The 2,6-sialylgalactosides are typically involved in modulating immune responses mediated by B cells, while the 2,3-sialylgalactosides are generally involved in T cell mediated immune responses. Thus, the invention provides methods of modulating an immune response in a mammal by administering to the mammal a therapeutically effective amount of an agent which causes a reduction in the amounts of a sialylated galactoside present in the mammal. Methods are also provided for preparing the immune response modulating agents as well as various screening assays to identify suitable modulating agents. In addition, the present invention provides screening assays for identifying agents that interfere with synthesis of Siaα2,6Gal- and Siaα2,3Gal-containing oligosaccharides. Therapeutic and other uses for these compounds are also provided.

In some embodiments, the invention provides methods and compositions for inhibiting immune responses mediated by B lymphocytes. Such methods can involve interfering with the synthesis of Siaα2,6Gal-containing oligosaccharides, such as, for example, Siaα2,6Galβ1, 4GlcNAc ("Sia6LacNAc" trisaccharide). This trisaccharide, which is a counterligand for CD22 and other molecules, is found on asparagine-linked carbohydrate groups of lymphocyte cell surface glycoproteins such as, for example, IgM, CD45, and CD22. The invention is based, at least in part, on the discovery that by inhibiting activity of a glycosyltransferase (e.g., an ST6Gal sialyltransferase; EC 2.4.99.1 (for nomenclature of sialyltransferases, see, Tsuji et al. (1996) *Glycobiol.* 6: v–xiv)) that is responsible for the synthesis of this ligand, one can inhibit B lymphocyte-mediated immune responses. Thus, for example, the invention relates to blocking agents which inhibit the activity of glycosyltransferases involved in the synthesis of the Sia6LacNAc trisaccharide. Alternatively, one can administer an agent (e.g., a sialidase), which enzymatically cleaves the sialic acid residue from the Siaα2,6 galactosides.

In other embodiments, the invention provides methods of inhibiting immune responses that are mediated by T lymphocytes, in particular CD8+ cytolytic T lymphocytes. These methods typically involve interfering with the biosynthesis or stability of α2,3 sialylgalactosides. For example, one can administer to a mammal an agent that inhibits the biosynthesis or stability of a Siaα2,3Galβ1, 3GalNAc trisaccharide. The agent can inhibit the activity of a glycosyltransferase involved in biosynthesis of the α2,3 sialyl galactoside such as, for example, a sialyltransferase (e.g., ST3GalII sialyltransferase; EC 2.4.99.4). Again, one can also achieve the desired effect by administering an agent that cleaves a residue, e.g., sialic acid, from the α2,3 sialylgalactosides.

Inhibitors of Glycosyltransferases

In one embodiment, the methods involve reducing an immune response by inhibiting the enzymatic activity of glycosyltransferase polypeptides that are involved in synthesis of the α2,6- or α2,3-sialylgalactosides. The biology and biochemistry of enzymes involved in the biosynthesis of specific glycosides such as Siaα2,6 galactosides and Siaα2,3 galactosides have been extensively studied. For review, see, e.g., Datta and Paulson (1997) *Indian J. Biochem. Biophys.* 34: 157–65; Guo et al. (1997) *Appl. Biochem. Biotechnol.* 68: 1–20; Tsuji (1996) *J. Biochem.* (Tokyo) 120: 1–13.

Glycosyltransferases, the general group of enzymes that catalyze the synthesis of these moieties, catalyze the transfer of a monosaccharide from a glycosylnucleotide, the donor substrate, to an acceptor substrate. The acceptor substrate may be another glycosyl residue, a polypeptide, or a lipid, depending on the specificity of the transferase. See, e.g., Beyer et al. (1981) *Adv. in Enzym.* 52: 24. Glycosyltransferases are grouped into families based on the type of sugar residue transferred. For example, enzymes that transfer sialic acid are called sialyltransferases, those that transfer fucose are called "fucosyltransferases," and those that transfer sialic acids are termed "sialyltransferases." Sialyltransferases are a family of glycosyltransferase enzymes that add sialic acid residues during oligosaccharide diversification (for review, see, e.g., Harduin-Lepers et al. (1995) *Glycobiology* 5: 741–758). Sialic acid addition occurs in the Golgi apparatus and generally terminates further oligosaccharide chain elongation. In each family there are typically 10–15 different enzymes required to elaborate the diverse carbohydrate structures found on glycoproteins and glycolipids of animal cells. Each enzyme makes a defined structure based on the donor and acceptor substrates they utilize, and the anomeric linkage formed in the transfer reaction.

Preferably, the inhibitor is specific for the particular glycosyltransferase of interest, and the glycosyltransferase is one that is not required for synthesis of other oligosaccharides that are not involved in an immune response. In preferred embodiments, the target glycosyltransferase is a sialyltransferase, as these enzymes catalyze the addition of the terminal carbohydrate moiety to the oligosaccharides involved in immune responses. For example, one can administer an inhibitor of a β-galactose α-2,6-sialyltransferase (e.g., an ST6Gal sialyltransferase) to modulate immune responses mediated by B lymphocytes, or a β-galactose α-2,3-sialyltransferase (e.g., ST3GalII) to modulate cytotoxic T lymphocyte-mediated immune responses.

Having identified the target enzyme to be inhibited (e.g., a sialyltransferase), many approaches can be used to block its activity. Examples of agents capable of inhibiting enzyme activity include, immunoglobulins, suicide substrates, alkylating agents, and various substrate analogs. For a review, see Fersht, *Enzyme Structure and Mechanism* (2d ed. 1985). The methods of modulating immune responses by inhibiting glycosyltransferase activity can involve administering to a mammal a compound that is an analog of a substrate for the glycosyltransferase.

In some embodiments, the inhibitor is a sugar nucleotide or an analog of a donor substrate, e.g., an analog of sialic acid or CMP-sialic acid. As discussed above, the donor substrates of glycosyltransferases are sugar nucleotides, usually diphosphonucleosides. For example, uridine diphosphosugars are donor substrates for the formation of glycosides of glucose, galactose, N-acetylglucosamine, xylose, and glucuronic acid. Guanosine diphosphosugars are donor substrates for the synthesis of glycosides of mannose and fucose. The glycosides of the sialic acids are formed by transfer from cytidine monophosphosialic acid.

Using this knowledge, one of skill in the art can readily synthesize a number of sugar nucleotides which can then be tested to identify those capable of maximum inhibition of a specific enzyme. The term "sugar nucleotide" as used herein refers both to sugar nucleotides discussed above and to various analogs thereof that might be synthesized or isolated from natural sources. The number of variations on this structure is limitless. For instance, both the ester linkage between the sugar and phosphate and the anhydride linkage of the pyrophosphate are potential targets of enzymatic cleavage. Replacement of the O—P or C—O linkage with a more stable C-P bond provides nucleotide monophosphate or diphosphate sugar analogs that are more resistant to enzymatic degradation. Such compounds have the potential to selectively inhibit glycoprotein or glycolipid synthesis by acting as substrate analogs of a particular glycosyltransferase. See, e.g., Vaghefi, et al., *J. Med. Chem.* 30:1383–1391 (1987), and Vaghefi et al., *J. Med Chem.* 30:1391–1399 (1987). Glycosyltransferase inhibitors are also described, for example, in U.S. Pat. No. 5,461,143.

Another approach is to replace the monophosphate or diphosphate bridge between the sugar residue and the nucleoside moiety. For instance, the diphosphate bridge can be replaced with an isosteric —OCONHSO$_2$O— residue. See, Samarasa, et al., *J. Med. Chem.* 28:40–46 (1985).

Analogs of sugar nucleotides capable of inhibiting glycosylation have been used as antibiotics and antiviral agents. Examples of such compounds include 2-deoxy-D-glucose, which is transformed to either UDP-2dGlc or GDP-2dGlc and in that form inhibits glycosylation of glycoproteins in the viral envelope. DeClercq, *Biochem. J.* 205:1 (1982) which is incorporated herein by reference. Antibiotics such as tunicamycin and streptovirudin are also effective because of their ability to inhibit glycosylation. For instance, tunicamycin is an analog of UDP-GlcNAc, the donor substrate for N-acetylglucos-aminyltransferases. The replacement of diphosphate bridge with a carbon chain allows tunicamycin to cross the cell membrane but still readily bind the active site of the enzyme. The structure of these and related compounds provide one of skill in the art with direction in designing and synthesizing compounds with similar inhibitory effects in accordance with the present invention as described herein. Additional analogs of sialic acid sugar nucleotides that are useful in the methods of the invention include, for example CMP-quinic acid and derivatives thereof (Schaub et al. (1998) *Glycoconjugate J.* 15: 345–354).

Nucleotides are the byproduct of the reaction by which glycosyl residues are transferred to acceptor substrates.

Nucleotides have been found to competitively inhibit glycosyltransferase. Thus, various nucleotides and their analogs have potential as inhibitors of these enzymes. For example, CDP and CMP can be used to inhibit sialyltransferase activity.

In addition to the donor substrate analogs, analogs of acceptor substrates may also be used as inhibitors. Again, the skilled artisan will recognize a variety of possible structures that can be used. Because of the acceptor substrate specificity of sialyltransferases, specific inhibition of the sialyltransferase that recognizes the lactose substrate can be achieved. Ideally, the inhibitory compounds should be capable of acting as specific acceptor substrates for a given enzyme, even in the presence of other enzymes. In addition, the compound should be an efficient acceptor substrate. Thus, the $K_i$ of the inhibitor should be at least about $10^{-5}$ M, more preferably at least about $10^{-7}$ M. Examples of acceptor analogs that inhibit sialyltransferases are described in U.S. Pat. No. 5,441,932. Other suitable analogs for inhibition of Sia6Gal sialyltransferases include derivatives of LacNAc in which the galactose residue is replaced by 6-deoxygalactose. Similarly, Sia3Gal I sialyltransferases are inhibited by LacNAc derivatives in which the galactose residue is replaced by 3-deoxygalactose. The deoxygalactose-containing compounds bind to the respective sialyltransferases, but do not function as an acceptor.

Glycosyltransferases can also be inhibited by contacting acceptor substrates for the glycosyltransferase with a competing glycosyltransferase or glycosidase that converts the acceptor oligosaccharide into a different structure that does not function as an acceptor for the glycosyltransferase of interest. For example, one can inhibit ST6Gal sialyltransferase activity by contacting a Galβ1,4GlcNAc-containing oligosaccharide with an α1,2 fucosyltransferase (e.g., FucT I or FucT II), which make the oligosaccharide structure Fucα1,2Galβ1,4GlcNAc, or an α1,3 fucosyltransferase (e.g., FucT III, FucT IV) which synthesize the structure Galβ1,4(Fucα1,3)GlcNAc (Paulson et al. (1978) *J. Biol. Chem.* 253: 5617–5624). Neither of these fucosylated compounds are acceptors for an ST6Gal sialyltransferase. An ST3Gal I sialyltransferase can be inhibited by converting its Galβ1,3GalNAc-containing acceptor with an α1,2 fucosyltransferase (e.g., FucT I or FucT II) to form Fucα1,2Galβ1,3GalNAc. This fucosylated oligosaccharide structure is not susceptible to addition of sialic acid at the 3 position of the galactose residue.

Naturally occurring molecules which show inhibitory effects may also be isolated for use in the present invention. The biosynthesis of glycoproteins or glycolipids is a complex metabolic pathway that depends on many factors for regulation. Naturally occurring inhibitory compounds can be purified and used to further inhibit activity. Ammonium chloride and chloroquine also have been reported to inhibit sialyltransferase activity (Thorens et al. (1986) *Nature* 321: 618).

The preferred glycosyltransferase inhibitors of the present invention have the ability to cross the cell membrane and enter the Golgi apparatus. Thus, the blocking agents are preferably sufficiently hydrophobic to allow diffusion through the membrane. Generally, they have no other adverse effects on cellular metabolism, so that other glycosylation reactions proceed while the specific reaction is inhibited. The blocking agents are preferably relatively small molecules, thereby avoiding immunogenicity and allowing passage through the cell membrane. Ideally, they have a molecular weight of between about 100–2000 daltons, but may have molecular weights up to 5000 or more, depending upon the desired application. In most preferred embodiments, the inhibitors have molecular weights of between about 200–600 daltons.

The inhibitors of the present invention preferably have strong affinity for the target enzyme, so that at least about 70% inhibition of glycosyltransferase activity is achieved, more preferably about 75%–85% and most preferably 90%–95% or more. The affinity of the enzyme for the inhibitor is preferably sufficiently strong that the dissociation constant, or $K_i$, of the enzyme-inhibitor complex is less than about $10^{-5}$ M, typically between about $10^{-6}$ and $10^{-8}$ M.

Yet another tactic to inhibit glycosyltransferase activity is to use immunoglobulin molecules raised against the particular enzyme of interest. See, e.g., White et al., *Biochem.*, 29:2740–2747 (1990). Thus, the multitude of techniques available to those skilled in the art for production and manipulation of various immunoglobulin molecules can be applied to inhibit intercellular adhesion. The immunoglobulins may exist in a variety of forms besides antibodies, including for example, Fv, Fab, and F(ab)$_2$, as well as in single chains.

Antibodies which bind the enzyme may be produced by a variety of means. The production of non-human monoclonal antibodies, e.g., murine, lagomorpha, equine, etc., is well known and may be accomplished by, for example, immunizing the animal with glycosyltransferase or a fragment thereof conjugated to a carrier. Antibody-producing cells obtained from the immunized animals are immortalized and screened, or screened first for the production of antibody which inhibits the interaction of the enzyme with the substrate and then immortalized. For a discussion of general procedures of monoclonal antibody production, see, Harlow and Lane, *Antibodies, A Laboratory Manual* (1988).

Enzyme inhibition generally involves the interaction of a substance with an enzyme so as to decrease the rate of the reaction catalyzed by that enzyme. Inhibitors can be classified according a number of criteria. For example, they may be reversible or irreversible. An irreversible inhibitor dissociates very slowly, if at all, from its target enzyme because it becomes very tightly bound to the enzyme, either covalently or noncovalently. Reversible inhibition, in contrast, involves an enzyme-inhibitor complex which may dissociate.

Inhibitors can also be classified according to whether they are competitive, noncompetitive or uncompetitive inhibitors. In competitive inhibition for kinetically simple systems involving a single substrate, the enzyme can bind either the substrate or the inhibitor, but not both. Typically, competitive inhibitors resemble the substrate or the product(s) and bind the active site of the enzyme, thus blocking the substrate from binding the active site. A competitive inhibitor diminishes the rate of catalysis by effectively reducing the affinity of the substrate for the enzyme. Typically, an enzyme may be competitively inhibited by its own product because of equilibrium considerations. Since the enzyme is a catalyst, it is in principle capable of accelerating a reaction in the forward or reverse direction.

Noncompetitive inhibitors allow the enzyme to bind the substrate at the same time it binds the inhibitor. A noncompetitive inhibitor acts by decreasing the turnover number of an enzyme rather than diminishing the proportion of free enzyme. Another possible category of inhibition is mixed or uncompetitive inhibition, in which the inhibitor affects the binding site and also alters the turnover number of the enzyme. Enzyme inhibition of kinetically complex systems involving more than one substrate, as is the case for glycosyltransferases, are described in Segel, *Enzyme Kinetics,* (Wiley, N.Y. 1975).

Screening methods for identifying blocking agents

One can identify therapeutically effective blocking agents by screening a variety of compounds and mixtures of compounds for their ability to inhibit glycosyltransferase activity. The use of screening assays to discover naturally occurring compounds with desired activities is well known and has been widely used for many years. For instance, many compounds with antibiotic activity were originally identified using this approach. Examples of such compounds include monolactams and aminoglycoside antibiotics. Compounds which inhibit various enzyme activities have also been found by this technique, for example, mevinolin, lovastatin, and mevacor, which are inhibitors of hydroxymethylglutamyl Coenzyme A reductase, an enzyme involved in cholesterol synthesis. Antibiotics that inhibit glycosyltransferase activities, such as tunicamycin and streptovirudin have also been identified in this manner.

Thus, another important aspect of the present invention is directed to methods for screening samples for glycosyltransferase inhibiting activity. A "sample" as used herein may be any mixture of compounds suitable for testing in a glycosyltransferase assay. A typical sample comprises a mixture of synthetically produced compounds or alternatively a naturally occurring mixture, such as a cell culture broth. Suitable cells include any cultured cells such as mammalian, insect, microbial or plant cells. Microbial cell cultures are composed of any microscopic organism such as bacteria, protozoa, yeast, fungi and the like.

In the typical screening assay, a sample, such as a fungal broth, is added to a standard glycosyltransferase assay. If inhibition of activity as compared to control assays is found, the mixture is usually fractionated to identify components of the sample providing the inhibiting activity. The sample is fractionated using standard methods such as ion exchange chromatography, affinity chromatography, electrophoresis, ultrafiltration, HPLC and the like. See, e.g., *Protein Purification, Principles and Practice,* (Springer-Verlag, 1982). Each isolated fraction is then tested for inhibitory activity. If desired, the fractions are then further subfractionated and tested. This subfractionation and testing procedure can be repeated as many times as desired.

By combining various standard purification methods, a substantially pure compound suitable for in vivo therapeutic testing can be obtained. A substantially pure blocking agent as defined herein is an inhibitory compound which migrates largely as a single band under standard electrophoretic conditions or largely as a single peak when monitored on a chromatographic column. More specifically, compositions of substantially pure blocking agents will comprise less than ten percent miscellaneous compounds.

Fucosyltransferase activity and its inhibition is typically assayed according to standard methods for determining enzyme activity. For a general discussion of enzyme assays, see, Rossomando, "Measurement of Enzyme Activity" in *Guide to Protein Purification,* Vol. 182, Methods in Enzymology (Deutscher ed., 1990).

An assay for sialyltransferase activity typically contains a buffered solution adjusted to physiological pH, a source of divalent cations, a donor substrate (usually labelled CMP-sialic acid), an acceptor substrate (e.g., LacNAc or Galβ1, 3GalNAc), sialyltransferase (typically ST6Gal or ST3Gal), and the sample or fraction of a sample whose inhibitory activity is to be tested. After a predetermined time at 23° C. or 37° C., the reaction is stopped and the sialylated product is isolated and measured according to standard methods (e.g., in a scintillation counter). Sialyltransferase assays which use a UV-labeled acceptor and lead to a UV-labeled product that can be readily separated by reverse phase HPLC and quantitated by UV spectroscopy are described in Schaub et al. (1998) *Glycoconjugate J.* 15: 345–354.

In addition to assaying for an effect on sialyltransferase activity to identify suitable modulators of immune responses, one can test directly for an effect on immune system function. Suitable assays include, for example, B cell proliferation assays, CTL activation assays, and the like. Assays are described herein, and also in, for example, Hennet et al. (1998) *Proc. Nat'l. Acad. Sci. USA* 95: 4504–4509.

Inhibition of Glycosyltransferase Gene Expression

Inhibition of glycosyltransferase gene expression can be achieved through the use of inhibitory nucleic acids. Inhibitory nucleic acids can be single-stranded nucleic acids that can specifically bind to a complementary nucleic acid sequence. By binding to the appropriate target sequence, an RNA-RNA, a DNA-DNA, or RNA-DNA duplex or triplex is formed. These nucleic acids are often termed "antisense" because they are usually complementary to the sense or coding strand of the gene, although recently approaches for use of "sense" nucleic acids have also been developed. The term "inhibitory nucleic acids" as used herein, refers to both "sense" and "antisense" nucleic acids.

In one embodiment, the inhibitory nucleic acid can specifically bind to a target nucleic acid that encodes an ST6Gal sialyltransferase. Administration of such inhibitory nucleic acids can inhibit B lymphocyte-mediated immune responses by reducing or eliminating the biosynthesis of Siaα2,6Gal-containing oligosaccharides. Nucleotide sequences encoding ST6Gal I are known for several species, including human (Grundmann et al (1990) *Nucl. Acids Res.* 18:667 (Genbank Accession No. X17247), European Patent 475354 (GenBank Accession No. A17362), Stamenkovich et al., *J. Exp. Med.* 172:641–643(1990) (GenBank Accession No. X54363)); chicken (Kurosawa et al. (1994) *Eur. J. Biochem.* 219:375–381 (EMBL Accession No. X75558)); rat (Weinstein et al. (1987) *J. Biol. Chem.* 262:17735–17743 (EMBL Accession No. M18769)); and mouse (Hamamoto et al. (1993) *Bioorg. Med. Chem.* 1: 141–145 (GenBank Accession No. D16106)). From these nucleotide sequences, one can derive a suitable inhibitory nucleic acid.

Other embodiments of the invention involve administering an inhibitory nucleic acid that specifically hybridizes to a target nucleic acid that encodes an ST3Gal sialyltransferase, preferably an ST3Gal I sialyltransferase. These methods inhibit CTL-mediated immune responses by reducing or eliminating the biosynthesis of Siaα2,3Gal-containing oligosaccharides. Several nucleotide sequences for ST3Gal Ia sialyltransferases from various species are known, such as chicken (Kurosawa et al. (1995) *Biochem. Biophys. Acta* 1244: 216–222 (GenBank Accession No. X80503)), human (Chang & Lau (1995) *Glycobiology* 5:319–325 (GenBank Accession No. L13972); Kitagawa & Paulson (1994) *J. Biol. Chem.* 269: 17872–17878 (GenBank Accession No. L29555)), mouse (Lee et al. (1993) *Eur. J. Biochem.* 216: 377–385 (GenBank Accession No. X73523)), porcine (Gillespie et al. (1992) *J. Biol. Chem.* 267: 21004–21010 (GenBank Accession Nos. M97753, M98463)). ST3Gal Ib sialyltransferase sequences are described for mouse (Lee et al. (1994) *J. Biol. Chem.* 269:10028–10033 (GenBank Accession No. X76989)), rat (Lee et al. (1994) *J. Biol. Chem.* 269:10028–10033 (GenBank Accession No. X76988)).

Nucleotide sequences for other glycosyltransferases, e.g., β1,4-galactosyltransferases, involved in biosynthesis of Sia6LacNAc and Sia3Gal-moieties are also suitable targets for inhibitory nucleic acids; several such sequences are known (see, e.g., Masri et al (1988) *Biochem. Biophys. Res. Commun.* 157:657–663).

By binding to the target nucleic acid, the inhibitory nucleic acid can inhibit the function of the target nucleic acid. This could, for example, be a result of blocking DNA transcription, processing or poly(A) addition to mRNA, DNA replication, translation, or promoting inhibitory mechanisms of the cells, such as promoting RNA degradation. Inhibitory nucleic acid methods therefore encompass a number of different approaches to altering expression of specific genes that operate by different mechanisms. These different types of inhibitory nucleic acid technology are described in Helene, C. and Toulme, J. (1990) *Biochim. Biophys. Acta.,* 1049:99–125.

Inhibitory nucleic acid therapy approaches can be classified into those that target DNA sequences, those that target RNA sequences (including pre-mRNA and mRNA), those that target proteins (sense strand approaches), and those that cause cleavage or chemical modification of the target nucleic acids.

Approaches targeting DNA fall into several categories. Nucleic acids can be designed to bind to the major groove of the duplex DNA to form a triple helical or "triplex" structure. Alternatively, inhibitory nucleic acids are designed to bind to regions of single stranded DNA resulting from the opening of the duplex DNA during replication or transcription. See Helene and Toulme, supra.

More commonly, inhibitory nucleic acids are designed to bind to mRNA or mRNA precursors. Inhibitory nucleic acids are used to prevent maturation of pre-mRNA. Inhibitory nucleic acids may be designed to interfere with RNA processing, splicing or translation. The inhibitory nucleic acids are often targeted to mRNA. In this approach, the inhibitory nucleic acids are designed to specifically block translation of the encoded protein. Using this approach, the inhibitory nucleic acid can be used to selectively suppress certain cellular functions by inhibition of translation of mRNA encoding critical proteins. For example, an inhibitory antisense nucleic acid complementary to regions of a target mRNA inhibits protein expression. See, e.g., Wickstrom E. L. et al. (1988) *Proc. Nat'l. Acad. Sci. USA* 85:1028–1032 and Harel-Bellan et al. (1988) *Exp. Med.,* 168:2309–2318. As described in Helene and Toulme, inhibitory nucleic acids targeting mRNA have been shown to work by several different mechanisms in order to inhibit translation of the encoded protein(s).

The inhibitory nucleic acids introduced into the cell can also encompass the "sense" strand of the gene or mRNA to trap or compete for the enzymes or binding proteins involved in mRNA translation. See Helene and Toulme.

Lastly, the inhibitory nucleic acids can be used to induce chemical inactivation or cleavage of the target genes or mRNA. Chemical inactivation can occur by the induction of crosslinks between the inhibitory nucleic acid and the target nucleic acid within the cell. Alternatively, irreversible photochemical reactions can be induced in the target nucleic acid by means of a photoactive group attached to the inhibitory nucleic acid. Other chemical modifications of the target nucleic acids induced by appropriately derivatized inhibitory nucleic acids may also be used.

Cleavage, and therefore inactivation, of the target nucleic acids may be effected by attaching a substituent to the inhibitory nucleic acid which can be activated to induce cleavage reactions. The substituent can be one that effects either chemical, photochemical or enzymatic cleavage. Alternatively cleavage can be induced by the use of ribozymes or catalytic RNA. In this approach, the inhibitory nucleic acids would comprise either naturally occurring RNA (ribozymes) or synthetic nucleic acids with catalytic activity.

In other embodiments, expression of glycosyltransferase genes is inhibited by administration of an agent that blocks the ability of a transactivating factor to induce gene expression. For example, one can administer an agent that interferes with the transactivating activity of tumor necrosis factor-alpha, interleukin-1, glucocorticoids (e.g., dexamethasone), retinoic acid, and some liver transcription factors (e.g., HNF-1, DBP and LAP).

The targeting of inhibitory nucleic acids to specific cells of the immune system by conjugation with targeting moieties binding receptors on the surface of these cells can be used for all of the above forms of inhibitory nucleic acid therapy.

Therapeutic and Diagnostic Uses of the Invention

The compositions and methods of the present invention can be used therapeutically to selectively inhibit glycosyltransferase activity (e.g., sialyltransferase) associated with a variety of immune responses. In some embodiments, the immune responses involve lymphoid cells, and often do not involve immune cells other than neutrophils. The invention can be used to inhibit deleterious immune responses associated with autoimmune disease, graft rejection and allergies. Inappropriate activation of the immune system is a component of a number of immunopathologies, such as autoimmunity, allograft rejection and allergic responses. Exemplary autoimmune diseases include rheumatoid arthritis, multiple sclerosis, and myasthenia gravis. Allergic responses include allergies to various pollens, dust mites and the like. In addition, foreign infectious diseases may cause immunopathology (e.g., lyme disease, hepatitis, LCMV, post-streptococcal endocarditis, or glomerulonephritis). Food hypersensitivities, such as celiac disease and Crohn's disease, as well as other allergic diseases, have been associated with inappropriate immune responses or suspected of having an autoimmune component.

Some embodiments of the invention are directed to methods of modulating immune responses that are mediated by B lymphocytes, e.g., humoral immunity. These immune responses, in which antibodies recognize and eliminate antigens, are the principal defense mechanism against extracellular microbes and their secreted toxins. B lymphocyte-mediated immune responses are inhibited by interfering with the biosynthesis of, or blocking, α2,6 sialyl galactosides.

Other embodiments of the invention provide methods of modulating immune responses that are mediated by T lymphocytes, in particular CD8$^+$ cytotoxic T lymphocytes. Such immune responses provide defense against infections by intracellular microbes such as viruses and some bacteria, which proliferate inside host cells and thus are inaccessible to circulating antibodies. CTL responses are inhibited by interfering with biosynthesis of, or blocking, α2,3sialylgalactosides.

In therapeutic applications, the glycosyltransferase inhibitors of the invention are administered to an individual already suffering from an inappropriate or undesirable immune response. Compositions that contain glycosyltransferase inhibitors or agents that bind to and block the α2,3- or α2,6 sialylgalactosides are administered to a patient in an amount sufficient to suppress the undesirable immune response and to cure or at least partially arrest symptoms and/or complications. An amount adequate to accomplish this is defined as "therapeutically effective dose." Amounts effective for this use will depend on, e.g., the inhibitor composition, the manner of administration, the stage and severity of the disease being treated, the weight and general state of health of the patient, and the judgment of the prescribing physician.

Alternatively, DNA or RNA that inhibits expression of one or more glycosyltransferase inhibitors, such as an anti-sense nucleic acid or a nucleic acid that encodes a peptide that blocks expression or activity of a glycosyltransferase can be introduced into patients to achieve inhibition. U.S. Pat. No. 5,580,859 describes the use of injection of naked nucleic acids into cells to obtain expression of the genes which the nucleic acids encode.

Therapeutically effective amounts of the glycosyltransferase inhibitor compositions of the present invention generally range for the initial immunization (that is for therapeutic or prophylactic administration) from about 1.0 mg to about 10 g of glycosyltransferase inhibitor for a 70 kg patient, usually from about 10 mg to about 5 g, and preferably between about 2 mg and about 1 g. These doses can be followed by repeated administrations over weeks to months depending upon the patient's response and condition by measuring immune system activity.

It must be kept in mind that the compositions of the present invention may be employed in serious disease states, that is, life-threatening or potentially life threatening situations. In such cases, in view of the minimization of extraneous substances and the relative nontoxic nature of the inhibitors, it is possible and may be felt desirable by the treating physician to administer substantial excesses of these compositions.

For prophylactic use, administration should be given to risk groups. Therapeutic administration may begin at the first sign of disease or the detection or shortly after diagnosis in the case of immune disorder. This is often followed by repeated administration until at least symptoms are substantially abated and for a period thereafter.

The pharmaceutical compositions for therapeutic or prophylactic treatment are intended for parenteral, topical, oral or local administration. Typically, the pharmaceutical compositions are administered parenterally, e.g., intravenously, subcutaneously, intradermally, or intramuscularly. Compositions of the invention are also suitable for oral administration. Thus, the invention provides compositions for parenteral administration which comprise a solution of the glycosyltransferase inhibiting agent dissolved or suspended in an acceptable carrier, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of glycosyltransferase inhibiting agents of the invention in the pharmaceutical formulations can vary widely, ie., from less than about 0.1%, usually at or at least about 2% to as much as 20% to 50% or more by weight, and will be selected primarily by fluid volumes, viscosities, etc., in accordance with the particular mode of administration selected.

The glycosyltransferase inhibitors of the invention may also be administered via liposomes, which serve to target the conjugates to a particular tissue, such as lymphoid tissue, or targeted selectively to infected cells, as well as increase the half-life of the peptide composition. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired peptide or conjugate of the invention can be directed to the site of lymphoid cells, where the liposomes then deliver the selected glycosyltransferase inhibitor compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., *Ann. Rev. Biophys. Bioeng.* 9:467 (1980), U.S. Pat. Nos. 4,235,871, 4,501,728 and 4,837,028.

The targeting of liposomes using a variety of targeting agents is well known in the art (see, e.g., U.S. Pat. Nos. 4,957,773 and 4,603,044). For targeting to the immune cells, a ligand to be incorporated into the liposome can include, e.g., antibodies or fragments thereof specific for cell surface determinants of the desired immnune system cells. A liposome suspension containing a peptide or conjugate may be administered intravenously, locally, topically, etc. in a dose which varies according to, inter alia, the manner of administration, the conjugate being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more conjugates of the invention, and more preferably at a concentration of 25%–75%.

For aerosol administration, the inhibitors are preferably supplied in a suitable form along with a surfactant and propellant. Typical percentages of glycosyltransferase inhibitors are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. The balance of the composition is ordinarily propellant. A carrier can also be included, as desired, as with, e.g., lecithin for intranasal delivery.

The present invention also provides methods of monitoring immune function by detecting the levels of α2,3 sialylgalactosides (to monitor CTL immune system function) and α2,6 sialylgalactosides (to monitor humoral immune system function) in a sample from a patient. This can be performed according to standard methods for detection of desired acarbohydrate structures. For instance, specific lectins or antibodies raised against the ligand can be used. For example, to detect levels of α2,6 sialylgalactosides, the lectin *Sambucus nigra* bark agglutinin (SNA), which can be isolated from the inner bark (bast tissue) of elder stems and branches or obtained commercially (Sigma Chemical Co., St. Louis Mo.), has an affinity for NeuNAc-α2-6-Gal, NeuNAc-α2-6-GalNAc, and, to a lesser extent, NeuNAc-[2-3]-Gal (Shibuya et al. (1987) *J. Biol. Chem.* 262: 1596). CD22 or a moiety having the Sia6LacNAc binding activity of CD22 can also be used to detect the presence or absence of Sia6LacNAc. Immune disorders that involve CTLs can be detected using an agent that binds to α2,3 sialylgalactosides. One example of a suitable binding agent for α2,3 is the MAL II lectin, which can be isolated from *Maackia amurensis* seeds.

Glycosyltransferases themselves, in particular the acceptor binding domain of a glycosyltransferase, are also useful as binding moieties in the diagnostic assays of the invention. In the absence of a particular sialyltransferase, for example, the concentration of acceptor moieties tends to increase. As an example, a deficiency of ST6Gal sialyltransferase causes a dramatic increase in terminal galactose residues (i.e., Galβ1,4GlcNAc-) on B cells. Thus, one can use the ST6Gal sialyltransferase as a detection moiety to determine whether ST6Gal is deficient in the cells. An ST3Gal transferase can be used similarly as a detection moiety.

In typical embodiments, the detection moieties are labeled with a detectable label. The detectable labels can be primary labels (where the label comprises an element that is detected directly or that produces a directly detectable element) or secondary labels (where the detected label binds to a primary label, as is common in immunological labeling). An introduction to labels, labeling procedures and detection of labels is found in Polak and Van Noorden (1997) *Introduction to Immunocytochemistry,* 2nd ed., Springer Verlag, N.Y. and in Haugland (1996) *Handbook of Fluorescent Probes and Research Chemicals,* a combined handbook and catalogue published by Molecular Probes, Inc., Eugene, Oreg. Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horse radish peroxidase, alkaline phosphatase etc.), spectral colorimetric labels such as colloidal gold or colored glass or plastic (e.g. polystyrene, polypropylene, latex, etc.) beads. The label may be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions.

Preferred labels include those that use: 1) chemiluminescence (using horseradish peroxidase or luciferase) with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored precipitate [kits available from Life Technologies/Gibco BRL, and Boehringer-Mannheim]); 3) hemifluorescence using, e.g., alkaline phosphatase and the substrate AttoPhos [Amersham] or other substrates that produce fluorescent products, 4) fluorescence (e.g., using Cy-5 [Amersham]), fluorescein, and other fluorescent tags]; 5) radioactivity. Other methods for labeling and detection will be readily apparent to one skilled in the art.

Preferred enzymes that can be conjugated to detection reagents of the invention include, e.g., luciferase, and horse radish peroxidase. The chemiluminescent substrate for luciferase is luciferin. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl) spiro[1,2-dioxetane-3,2'-adamantane], which is detected with a luminometer. Embodiments of horse radish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected with a spectrophotometer; and 3,3,5,5'-tetramethylbenzidine (TMB), 3,3'diaminobenzidine (DAB), 3-amino-9-ethylcarbazole (AEC), and 4-chloro-1-naphthol (4C1N), which are detected visually. Other suitable substrates are known to those skilled in the art.

In general, a detector which monitors a particular label is used to detect the label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

Commercially available detection moieties that are suitable for use in the methods of the invention include SNA-fluorescein isothiocyanate (FITC) lectin (FL-1301, Vector Laboratories, Burlingame Calif.) and biotinylated SNA lectin (B-1305, Vector Laboratories) for α2,3 sialyl galactosides. For detection of α2,6 sialylgalactosides, MAL II-FITC lectin and biotinylated MAL II lectin (B-1265, Vector Laboratories) are examples of suitable detection moieties.

Immunodeficiency is indicated by a substantial reduction of α2,3- or α2,6-sialylgalactosides in a sample, e.g., lymphocytes, obtained from the patient. Alternatively, methods for detecting levels of specific glycosyltransferase activities can be used. Standard assays for detecting glycosyltransferases such as the ST6Gal and ST3Gal I are described herein. Again, immunodeficiency is indicated by a substantial reduction in activity of the particular glycosyltransferase. As used herein, a "substantial reduction" in the appropriate sialylgalactoside levels or glycosyltransferase activity refers to a reduction of at least about 30% in the test sample compared to a non-immunodeficient control. Preferably, the reduction will be at least about 50%, more preferably at least about 75%, and most preferably sialylgalactoside or glycosyltransferase levels will be reduced by at least about 90% in a sample from an immunodeficient mammal compared to a non-immunodeficient control.

Transgenic Animals that Lack ST6Gal Sialyltransferase or ST3Gal Sialyltransferase The invention also provides chimeric and transgenic nonhuman animals which contain cells that lack at least one sialyltransferase gene that is found in wild-type cells of the animal, and methods for producing such animals. Of particular interest are chimeric and transgenic animals that lack either an ST6Gal sialyltransferase gene or an ST3GalII sialyltransferase gene. These animals are useful for several purposes, including the study of the mechanisms by which sialylated oligosaccharides influence immune responses and other effects. Such "knockout" animals can also be used for producing glycoproteins and glycolipids that, when produced in a wild-type animal, would carry a sialic acid residue that is not desirable for a particular application.

A "chimeric animal" includes some cells that lack the functional sialyltransferase gene of interest and other cells that do not have the inactivated gene. A "transgenic animal," in contrast, is made up of cells that have all incorporated the specific modification which renders the sialyltransferase gene inactive. While a transgenic animal is capable of transmitting the inactivated sialyltransferase gene to its progeny, the ability of a chimeric animal to transmit the mutation depends upon whether the inactivated gene is present in the animal's germ cells. The modifications that inactivate the sialyltransferase gene can include, for example, insertions, deletions, or substitutions of one or more nucleotides. The modifications can interfere with transcription of the gene itself, with translation and/or stability of the resulting mRNA, or can cause the gene to encode an inactive sialyltransferase polypeptide.

The claimed methods are useful for producing transgenic and chimeric animals of most vertebrate species. Such species include, but are not limited to, nonhuman mammals, including rodents such as mice and rats, rabbits, ovines such as sheep and goats, porcines such as pigs, and bovines such as cattle and buffalo. Methods of obtaining transgenic animals are described in, for example, Puhler, A., Ed., *Genetic Engineering of Animals,* VCH Publ., 1993; Murphy and Carter, Eds., *Transgenesis Techniques: Principles and Protocols* (*Methods in Molecular Biology,* Vol. 18), 1993; and Pinkert, C. A., Ed., *Transgenic Animal Technology: A Laboratory Handbook,* Academic Press, 1994.

One method of obtaining a transgenic or chimeric animal having an inactivated sialyltransferase gene in its genome is to contact fertilized oocytes with a vector that includes a sialyltransferase-encoding polynucleotide that is modified to contain an inactivating modification. For some animals, such as mice, fertilization is performed in vivo and fertilized ova are surgically removed. In other animals, particularly bovines, it is preferably to remove ova from live or slaughterhouse animals and fertilize the ova in vitro. See DeBoer et al., WO 91/08216. In vitro fertilization permits the modifications to be introduced into substantially synchronous cells. Fertilized oocytes are then cultured in vitro until a pre-implantation embryo is obtained containing about 16–150 cells. The 16–32 cell stage of an embryo is described as a morula. Pre-implantation embryos containing more than 32 cells are termed blastocysts. These embryos show the development of a blastocoel cavity, typically at the 64 cell stage. If desired, the presence of a desired inactivated sialyltransferase gene in the embryo cells can be detected by methods known to those of skill in the art. Methods for culturing fertilized oocytes to the pre-implantation stage are described by Gordon et al. (1984) *Methods Enzymol.* 101: 414; Hogan et al. *Manipulation of the Mouse Embryo: A Laboratory Manual,* C.S.H.L. N.Y. (1986) (mouse embryo); Hammer et al. (1985) *Nature* 315: 680 (rabbit and porcine embryos); Gandolfi et al. (1987) *J. Reprod. Fert.* 81: 23–28; Rexroad et al. (1988) *J. Anim. Sci.* 66: 947–953 (ovine embryos) and Eyestone et al. (1989) *J. Reprod. Fert.* 85: 715–720; Camous et al. (1984) *J. Reprod. Fert.* 72: 779–785; and Heyman et al. (1987) *Theriogenology* 27: 5968 (bovine embryos). Sometimes pre-implantation embryos are stored frozen for a period pending implantation. Pre-implantation embryos are transferred to an appropriate female resulting in the birth of a transgenic or chimeric animal depending upon the stage of development when the transgene is integrated. Chimeric mammals can be bred to form true germline transgenic animals.

Alternatively, the modified sialyltransferase gene can be introduced into embryonic stem cells (ES). These cells are obtained from preimplantation embryos cultured in vitro. See, e.g., Hooper, M L, *Embryonal Stem Cells: Introducing Planned Changes into the Animal Germline* (Modern Genetics, v. 1), Int'l. Pub. Distrib., Inc., 1993; Bradley et al. (1984) *Nature* 309,255–258. Transformed ES cells are combined with blastocysts from a nonhuman animal. The ES cells colonize the embryo and in some embryos form the germ line of the resulting chimeric animal. See, Jaenisch (1988) *Science* 240: 1468–1474. Alternatively, ES cells or somatic cells that can reconstitute an organism ("somatic repopulating cells") can be used as a source of nuclei for transplantation into an enucleated fertilized oocyte giving rise to a transgenic mammal. See, e.g., Wilmut et al. (1997) *Nature* 385: 810–813.

The introduction of the modified sialyltransferase gene into recipient cells can be accomplished by methods known to those of skill in the art. For example, the modified gene can be targeted to the wild type sialyltransferase locus by homologous recombination. Alternatively, a recombinase system can be employed to delete all or a portion of a locus of interest. Examples of recombinase systems include, the cre/lox system of bacteriophage P1 (see, e.g., Gu et al. (1994) *Science* 265: 103–106; Terry et al. (1997) *Transgenic Res.* 6: 349–356) and the FLP/FRT site specific integration system (see, e.g., Dymecki (1996) *Proc. Nat'l. Acad. Sci. USA* 93: 6191–6196). In these systems, sites recognized by the particular recombinase are typically introduced into the genome at a position flanking the portion of the gene that is to be deleted. Introduction of the recombinase into the cells then catalyzes recombination which deletes from the genome the polynucleotide sequence that is flanked by the recombination sites. If desired, one can obtain animals in which only certain cell types lack the sialyltransferase gene of interest. See, e.g., Tsien et al. (1996) *Cell* 87: 1317–26; Brocard et al. (1996) *Proc. Nat'l. Acad. Sci. USA* 93: 10887–10890; Wang et al. (1996) *Proc. Nat'l. Acad Sci. USA* 93: 3932–6; Meyers et al. (1998) *Nat. Genet.* 18: 13641).

The following examples are offered to illustrate, but not to limit the present invention.

EXAMPLE 1

Construction and Analysis of Transgenic Mice Deficient in ST6Gal Sialyltransferase The following example demonstrates that inhibition of sialyltransferase activity associated with the synthesis of Sia6LacNAc leads to suppression of the immune system in mice. Mice deficient in Sia6LacNAc were created by deletion of the sialyltransferase gene responsible for its synthesis, ST6Gal I. Mice deficient in ST6Gal I appeared normal in most respects, but exhibited hallmarks of profound immunosuppression. Notably, serum levels of IgM were significantly reduced, and the mice were markedly deficient in production of antibodies in response to immunization with T-independent and T-dependent antigens. As biochemical correlates of this phenotype, B lymphocytes were hyporresponsive to IgM and CD40 crosslinking. These studies reveal that the ST6Gal-I sialyltransferase and corresponding production of the Sia6LacNAc trisaccharide ligand of CD-22 is essential for normal B cell activation.

Materials and Methods

ST6Gal Gene Targeting

Mice harboring a mutated ST6Gal-I gene were generated from embryonic stem cells following a targeted deletion of ST6Gal-I exon 2 containing the N-terminal 200 amino acids of the encoded sialyltransferase. The ST6Gal I targeting vector was assembled from a 129/Sv genomic clone by inserting the 1.9 kb Acc I-Bam HI fragment containing exon 2 of ST6Gal I encoding the first 200 amino acids into the Bam HI site of the pflox vector. Adjacent 129/Sv ST6Gal I genomic sequences were added by subcloning the 1.8-kb Nhe I-Acc I fragment into the Sal I site and the Bam HI-Bam HI 12 kb fragment into the Hind III site of pflox, respectively. Ten $\mu$g of Not I-linearized targeting vector were electroporated into ES cells and G418 resistant transfectants (120 $\mu$g/ml), positive by PCR for homologous recombination and which retained all three loxP sites were transfected with Cre expression vector. Following four days of gancyclovir (2 $\mu$M) selection, subclones were isolated and those bearing either the ST6Gal$^F$ allele (B3) or the ST6Gal I$^\Delta$ allele (B9) were confirmed by Southern blotting with loxP and Hind III-Hind III genomic probes. B3 and B9 ES cells were used to generate chimeric mice in C57BL/6 host embryos. Offspring were genotyped by Southern blotting with Bgl II-digested tail DNA hybridized to the Hind III-Hind III 500 bp genomic probe. Heterozygous offspring were mated to C57BL/6 mates and the mutations were propagated in this strain for at least two generations before crosses to produce homozygotes for experimentation. The ST6Gal I mutation was maintained in the C57BL/6 inbred line for 3–5 generations prior to analyses (see, FIG. 1A). The phenotypes described were found linked to mice bearing the homozygous ST6Gal$^\Delta$ mutant phenotype in subsequent studies involving more than four generations. Mice homozygous for the ST6Gal$^F$ genotype did not display any phenotypic consequences and as expected contained normal levels of Sia6LacNAc.

Deletion of ST6Gal-I exon 2 results in loss of cytoplasmic, transmembrane and considerable catalytic domain sequences, such that any translated truncated enzyme would also be incapable of entry into the lumen of the endoplasmic reticulum and Golgi. Mice homozygous for the ST6Gal-I$^\Delta$ deletion were born at Mendelian frequency and appeared grossly normal throughout post-natal development.

Fluorescence-Activated Cell Sorter Analysis

ST6Gal-I function was assessed in assays using SNA and CD22-Ig lectins which specifically bind the Sia$\alpha$2-6Gal$\beta$1-4GlcNAc (Sia6LacNAc) trisaccharide found on various asparagine (N)-linked oligosaccharides. Single cell suspensions from the spleen, thymus, lymph node and bone marrow were subjected to ammonium chloride lysis of red cells. Cells were counted with a hemocytometer and 500,000 cells were labeled in a final volume of 100 $\mu$l with either SNA-FITC (5 $\mu$g/ml; Vector Laboratories), or MAL II-FITC (5 $\mu$g/ml; Vector Laboratories) and/or 1 $\mu$l of monoclonal antibody or CD22-Ig chimera for 10 minutes. All incubations and washes were performed on ice in FACS buffer (2% FCS in PBS). Cells were analyzed using a "FACScan" Flow Cytometer and Celiquest Software (Becton Dickinson). Serum isotype-specific antibody titres were determined by ELISA using plates coated with anti-mouse isotype specific antibodies. A standard curve was generated using purified mouse IgM, IgA (Sigma), and IgG$_1$ (PharMingen) to convert OD values to $\mu$g/ml. Antibodies and lectins used in the course of these and other studies herein included (all from PharMingen unless otherwise noted): anti-CD3 (2C11), anti-CD4 (RM4-5), anti-CD8 (53-6.7), anti-CD11b-FITC or -PE (Mac-1, M1/70), anti-CD21.35 (7G6), anti-CD22-PE (Cy34.1), anti-CD23 (B3B4), anti-CD43 (S7), anti-CD44 (IM7), anti-B7.2 (GI.1), antiB220-PE (RA3-6B2), anti-mouse IgM-biotin (II/41), anti-mouse IgD-FITC (11-26c.2a), anti-CD24 (HSA)-FITC (M1/69), anti-CD40-FITC (HM40-3), anti-CD19-FITC (1D3), anti-mouse I-A$^b$-FITC (AF6-120.1), anti-erythroid (Ter-119); anti class I MHC (KH95), anti-Ly-6G (Gr-1)-PE (RB6-8C5) (Pharmingen), SNA-FITC, ECA-FITC, and PNA-FITC (Vector Laboratories). In FACS analyses, biotinylated antibodies were detected using Streptavidin-Tri-Color (CalTag, South San Francisco Calif.). The CD22-hIg fusion chimera was as described in Stamenkovic et al., Cell, 66:1133 (1991).

ST6Gal Sialyltransferase Activity Measurements

Tissue samples were homogenized in 3 ml of 500 mM sucrose, 1 mM MgCl$_2$, 1% dextran, 5 mM 2-mercaptoethanol. After removal of cell debris at 10,000×g, membranes were isolated by centrifugation at 40,000 rpm in a Beckman SW50.1 rotor for 1 hr. Membranes were solubilized in 25 mM cacodylate buffer (pH 6.8)/2% Triton X-100 for 15 min on ice. The membrane and cytosolic fractions (12.5 $\mu$l) were analyzed for sialyltransferase activity in 25 $\mu$l assays with 25 mM cacodylate (pH 6.8), 0.4 mM CMP-sialic acid (Sigma), 10$^5$ cpm of CMP-[$^{14}$C]sialic acid (170 pmol) (Amersham), and 1 mM LacNAc-octyl. Reactions were incubated at 37° C. for 1 hr. Products were separated from unincorporated sialic acid by chromatography on Sep-Pak C$_{18}$ cartridges (Waters), dried by centrifugal evaporation, redissolved in 50 $\mu$l of 50 mM sodium citrate buffer (pH 6.0), and incubated for 1 hr at 37° C. after the addition of two units Salmonella typhimurium LT2 sialidase (New England Biolabs). The digestion products were applied to SepPak C$_{18}$ cartridges, washed with 15 ml of H$_2$O, and eluted with 5 ml of methanol. The amount of [$^{14}$C]sialic acid in the methanol eluates was measured in a liquid scintillation counter (RackBeta, Pharmacia). Separately, a recombinant soluble form of the human ST6Gal enzyme produced in Pichia pastoris was used in sialic acid transfer to the LacNAc-octyl acceptor and followed by the sialidase treatment described above. No significant cleavage was observed by loss of radiolabeling, thereby confirming the specificity of the LT2 sialidase for the $\alpha$2,3 linkage when used in the above conditions. ST6Gal activity measurements undertaken with cytosolic fractions did not reveal any significant activity in either wild-type (wt) or mutant extracts.

B Cell Proliferation Assays

B lymphocyte isolation was accomplished by subjecting splenocytes or lymph node cell suspensions to complement mediated lysis with anti-Thy 1.2 (Becton Dickinson), anti-Ly-6G (GR-1), and rabbit complement (Accurate Chemicals), followed by a cushion centrifugation onto NycoPrep (Life Technologies, Gaithersburg Md.) to remove debris and dead cells. Viable cells were identified by FACS as >90% B lymphocytes using anti-B220. Equivalent numbers of B cells of each genotype (1×10$^5$) were cultured in complete RPMI 1640 medium containing 2-mercaptoethanol (0.1 mM), 10% FCS, and L-glutamine with the indicated concentrations of goat F(ab')$_2$ anti-mouse IgM antiserum (Jackson, West Grove Pa.), anti-CD40 with or without IL4 (Genzyme), or lipopolysaccharide (LPS) (Sigma). Proliferation was measured by [$^3$H-thymidine incorporation (2.5 μCi per well) during the last 16 hr of a 64 hr assay period.

Calcium Measurements

Single cell suspensions of splenocytes were isolated and subjected to ammonium chloride red cell lysis. Cells were then counted using a hemocytometer and 10$^7$ cells were incubated with 10 μM Indo-1 AM ester (Molecular Probes) at 37° C. for 30 min in 1 ml of complete RPMI 1640 medium. Cells were washed in FACS buffer and stained with FITC-conjugated anti-B220 (PharMingen) for 10 min at room temperature, washed again and resuspended in 1 ml of complete RPMI 1640 medium containing 10 mM Hepes (pH 7.4). Two hundred microliters of this suspension was added to 750 μl of RPMI-Hepes medium and B220$^+$ cells were analyzed by FACS using a Coulter Elite (Coulter) with MULTITIME™ software (Phoenix Flow Systems, San Diego). Baseline fluorescence ratios (525/405 nm) were collected for one min before the addition of antibodies. The final concentrations of goat F(ab')$_2$ anti-mouse IgM used were 10 μg/ml and 30 μg/ml.

Protein Phosphotyrosine Analyses

Splenic B cells were isolated by complement-mediated lysis (see above) and 5×10$^5$ isolated B cells were resuspended in 50 μl of RPMI 1640 medium with 0.5% FCS. Cells were warmed to 37° C. before stimulation with 10 μl of goat F(ab')$_2$ anti-mouse IgM (120 μg/ml). At the indicated times, 15 μl of lysis buffer was added to give a final concentration of 1% Triton X-100, 50 mM Tris-HCl (pH 8.0), 150 mM NaCl, 1 mM EDTA, 10 mM NaF, 1 mM Na$_3$VO$_4$, 1 mM Na$_2$MoO$_4$, 2 μg/ml leupeptin, 2 μg/ml pepstatin, 2 μg/ml aprotinin, 5 μg/ml soybean trypsin inhibitor, and 40 μg/ml phenylmethylsulfonyl fluoride. Whole cell extracts representing 1×10$^5$ splenic B cells were run on a SDS/10% PAGE gel and transferred to nitrocellulose. Proteins phosphorylated on tyrosine were detected with monoclonal anti-phosphotyrosine antibody 4G10 (Upstate Biotechnology, Lake Placid N.Y.) by immunoblotting.

Immunizations and Serum Antibody Assays

Figure 4:
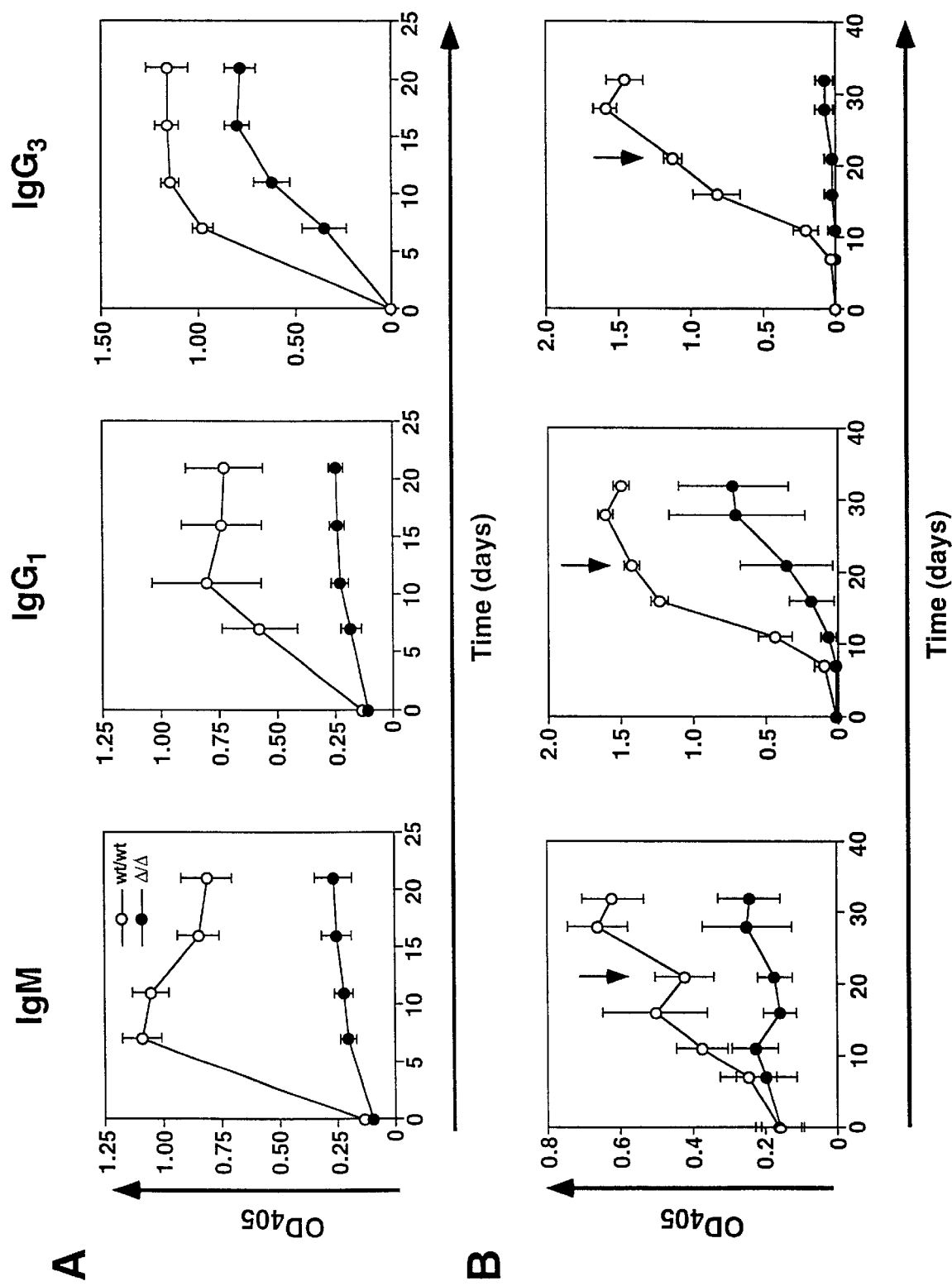
FIGS. 4A and 4B shows that antibody production is deficient following immunization of Sia6LacNAc deficient mice.

Mice were prebled to obtain preimmune sera and subsequently immunized by i.p. injection of either 10 μg or 100 μg of dinitrophenyl (DNP)-keyhole limpet hemocyanin (KLH) (Calbiochem) in Freund's complete adjuvant, or 0.1 μg or 10 μg of dNP-Ficoll (Biosearch) in PBS. Serum was collected at the indicated times and anti-DNP titers were determined by ELISA using plates coated with 20 μg of DNP-BSA and blocked with 10% FCS in PBS. Mice receiving the DNP-KLH antigen were boosted at the indicated times with the same amount of antigen in Freund's incomplete adjuvant. Sera were diluted to various concentrations and analyzed using anti-mouse isotype-specific antibodies conjugated to alkaline phosphatase (for IgM, Sigma; for IgG$_1$, Caltag; for IgG$_3$, Southern Biotechnology Associates). OD$_{405}$ values were obtained using a microplate reader (Molecular Devices). Results shown in FIG. 4 comprise the indicated sera dilution in the linear range for OD$_{405}$ values obtained.

Results

ST6Gal alleles were mutagenized in embryonic stem cells by homologous recombination and Cre recombinase action (FIG. 1A and FIG. 1B). To achieve a systematic mutation, exon 2 was chosen for deletion. This exon contains the N-terminal 200 amino acids and over 50% of the ST6Gal coding sequence. Deletion of exon 2 results in loss of cytoplasmic, transmembrane, and considerable catalytic domain sequences, such that any resulting stably translated, truncated, and active enzyme would be incapable of entry into the lumen of the endoplasmic reticulum and Golgi apparatus. Mice homozygous for the deleted ST6Gal$^Δ$ allele were born at normal frequency, were fertile, and did not exhibit abnormalities in weight or overt behavior (FIG. 1B and data now sown). Histologic studies of various tissues including liver, brain, kidney, spleen, and thymus were unremarkable. Additionally, a normal hematologic profile involving leukocytes, erythrocytes, and platelets was observed among peripheral blood samples. Enzymatic studies of liver and splenocyte extracts using the Galβ1-4GlcNAc-octyl acceptor (see Materials and Methods) revealed that mice homozygous for the ST6Gal$^Δ$ allele were deficient in ST6Gal activity (Table 1), indicating that the exon 2 deletion produced a null mutation.

TABLE 1

ST6Gal activity levels in membranes derived from wild-type (wt/wt) and homozygous-mutant (Δ/Δ) ST6Gal genotypes.

| | ST6Gal Activity, pmol/min per mg of protein | |
|---|---|---|
| Genotype | Liver | Splenocytes |
| wt/wt | 13.4 ± 1.0 | 33.1 ± 9.5 |
| Δ/Δ | 0.3 ± 0.1 | 0.3 ± 0.2 |

Expression of the ST6Gal product was assessed using the *Sambucus nigra*-derived lectin SNA and a recombinant soluble CD11-Ig lectin chimera, which both bind the Sia6LacNAc trisaccharide with high specificity (Powell et al. (1993) *J. Biol. Chem.* 268: 7019–7027; Sgroi et al. (1993) *J. Biol. Chem.* 268: 7011–7018; Powell & Varki (1994) *J. Biol. Chem.* 269: 10628–10636). In contrast to erythroid and myeloid cells analyzed, lymphocytes were found to highly express cell surface Sia6LacNAc (FIG. 1C). Lymphocytes from mice homozygous for the ST6Gal$^Δ$ mutation were deficient in binding to SNA and CD22-Ig, whereas mice homozygous for the loxP-flanked ST6Gal$^F$ allele expressed normal levels of Sia6LacNAc on their cell surfaces (FIG. 1C and data not shown). Levels of α2-3-linked sialic acids were visualized using the *Maackia amurensis*-derived lectin MAL II. No significant changes in α2-3-linked sialic acid levels were thereby observed among lymphoid cells isolated from mice homozygous for the ST6Gal$^Δ$ allele (FIG. 1C). Residual or low-level SNA and CD22-Ig binding may reflect the presence of Siaα2-6GalNAc on O glycans (Hanasaki et al. (1995) *J. Biol. Chem.* 270: 7533–7542), although it also remains possible that additional enzymes exist that product low levels of Sia6LacNAc. Nevertheless, the deletion generated in the ST6Gal locus results in loss of ST6Gal activity and a deficiency in Sia6LacNAc production at the cell surface, consistent with the described biochemical role of ST6Gal and its' inactivation in mice homozygous for the ST6Gal$^Δ$ allele.

Figure 2:
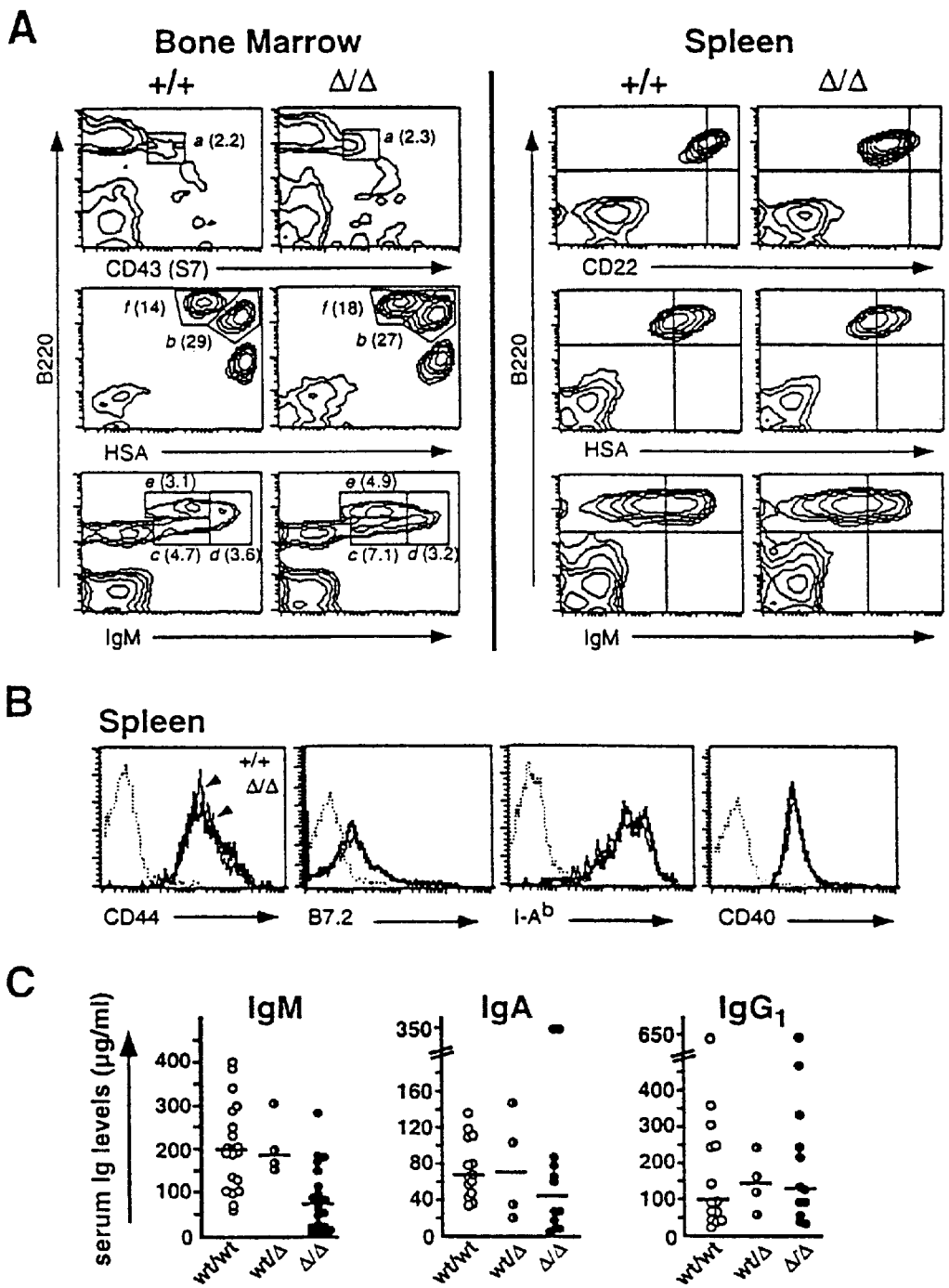
FIGS. 2A–2C show B lymphocyte characterization and serum immunoglobulin analyses.

Sia6LacNAc-deficient mice contained normal numbers of Gr-1$^+$ myeloid, Ter-119$^+$ erythroid, B220$^+$ B lymphoid, and T lymphoid (CD3$^+$, CD4$^+$, CD8$^+$) cells in the thymus, spleen, lymph nodes, and bone marrow. B lymphocyte development in the bone marrow of ST6Gal-deficient mice was unaltered. The percentage of pro-B cells in the ST6Gal-deficient bone marrow (B220$^{lo}$ CD43$^+$, Hardy et al. (1991) *J. Exp. Med.* 173: 1213–1225) was normal (FIG. 2A gate a). Furthermore, the frequency of immature B cells (B220$^{lo}$ IgM$^{int}$, Carsetti et al. (1995) *J. Exp. Med.* 181: 2129–2140) was not affected by ST6Gal inactivation (FIG. 2A, gates b and c). Similarly, no statistically significant changes were found in the abundance of mature B cells in the marrow (B220$^{hi}$ IgM$^{int}$ and B220$^{hi}$ HSA$^{lo}$, ref. Carsetti et al., supra.; FIG. 2A, gates e and f) or in the previously defined transitional B cell population undergoing maturation and negative selection (B220$^{lo-hi}$ IgM$^{hi}$, Carsetti et al., supra.; FIG. 2A, gate d).

Although B lymphocyte abundance and development appeared unaltered in Sia6LacNAc-deficient mice, their B cells invariably exhibited reductions in cell surface IgM and CD22. Although HSA levels were unaffected, ST6Gal deficiency resulted in peak IgM levels at 65% of controls and CD22 levels 38% of normal (FIG. 2A, Right). However, no evidence for B lymphocyte activation was found in analyses of cell surface activation markers CD44, B7.2, and major histocompatibility complex class II (I-A$^b$) (FIG. 2B). Additionally, CD40 expression was unaltered with ST6Gal deficiency (FIG. 2B). Additional analyses of splenic B cells from Sia6LacNAc-deficient mice revealed normal expression of cell surface CD19, CD21, CD23, and CD45RA$^+$ (B220) (data not shown).

Reductions observed in cell surface IgM and CD22 prompted analyses of serum Ig levels to initially assess B cell function in unimmunized mice. Sia6LacNAc-deficient mice exhibit significant decreases in IgM levels to a median value of 37% of normal while statistically unaltered levels of IgA and IgG were observed (FIG. 2C). Although Sia6LacNAc deficiency does not impede lymphocyte development of trafficking, dysfunctional B lymphocytes might reside in mice homozygous for the ST6Gal$^\Delta$ allele.

Figure 3:
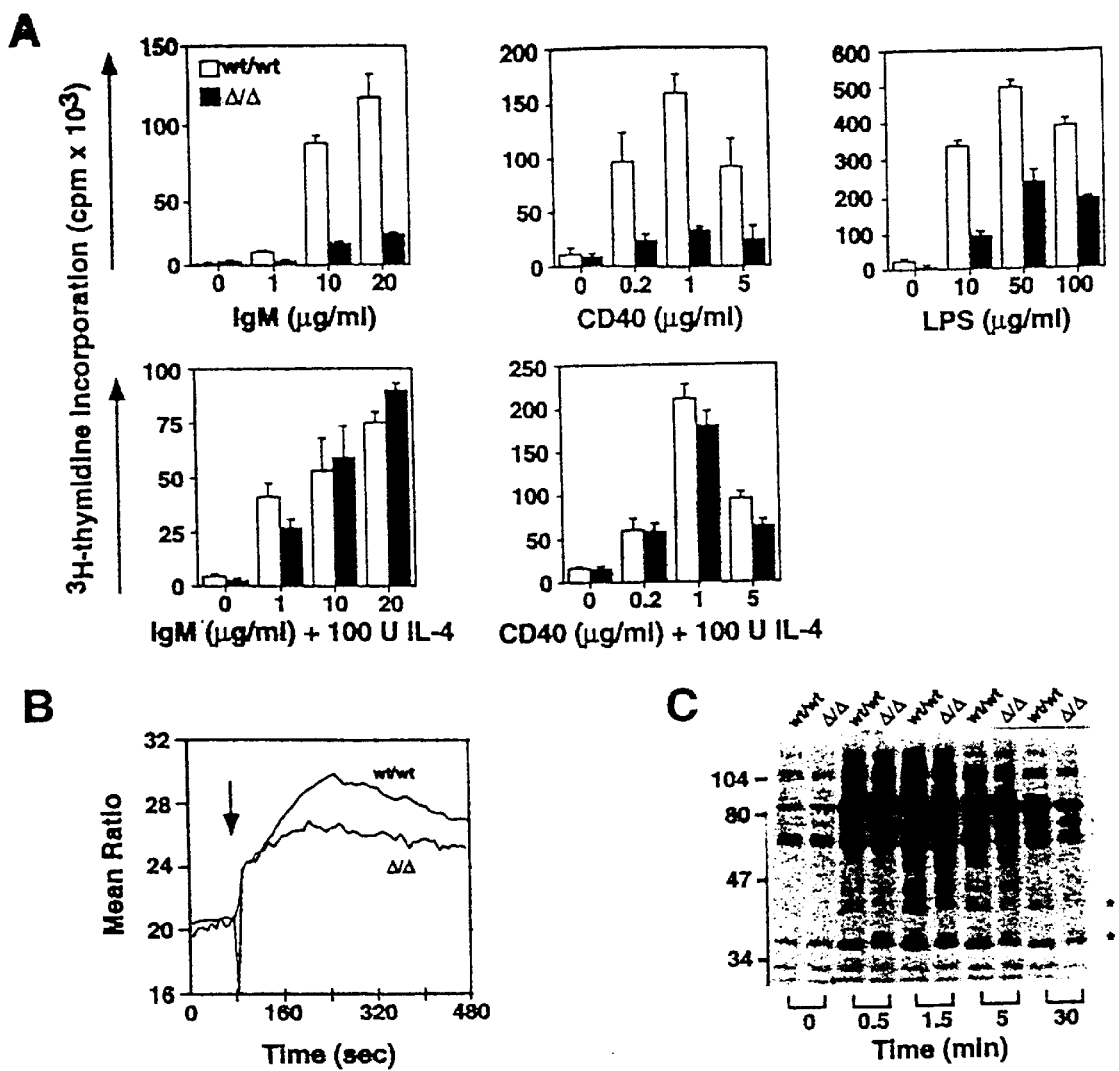
FIGS. 3A–3C demonstrate that B cell activation responses are attenuated in mice that are deficient in ST6Gal function.

B lymphocyte immune activation proceeds by increased tyrosine phosphorylation and Ca$^{2+}$ mobilization leading to gene activation and proliferation as necessary for effective humoral immunity (Campbell & Sefton (1990) *EMBO J.* 9: 2125–21312; Gold et al. (1990) *Nature* 345: 810–813; Plieman et al. (1994) *Immunol. Today* 15: 393–399; Cooke et al. (1994) *J. Exp. Med* 179: 425–438). B lymphocytes from control and ST6Gal-deficient mice were isolated from the spleen or lymph nodes and activated by crosslinking cell surface IgM, CD40, or by addition of LPS. Proliferation of ST6Gal-deficient B lymphocytes in response to these stimuli was found to be significantly reduced (FIG. 3A). Interestingly, normal responsiveness was observed when interleukin-4 (IL-4) was present during the stimulation as various and suboptimal concentrations of stimulatory anti-IgM or anti-CD40 antibodies. IL-4 promotes Ig class switching from IgM to IgG and IgE (Paul, W E (1991) *Blood* 77: 1859–1870; Coffmian et al. (1993) *Adv. Immunol.* 54: 229–270) and can synergize with suboptimal antigen-receptor activation likely through coactivation of "downstream" cytosolic and nuclear signal transduction events. Results observed with IL-4 reveal the intrinsic ability of ST6Gal-deficient B lymphocytes to respond normally in some conditions; however, activation of N lymphocytes through the antigen-receptor complex and following CD40 ligation is adversely affected.

The efficacy of early signal transduction events was assessed by measuring Ca$^{2+}$ mobilization and phosphotyrosine accumulation immediately following anti-IgM stimulation. Cytosolic mobilization of Ca$^{2+}$ from intracellular compartments occurs rapidly upon IgM crosslinking by hydrolysis of inositol phospholipids (Plieman et al., supra., Cooke et al., supra.). B lymphocytes from St6Gal null mice failed to mobilized Ca$^{2+}$ as efficiently as controls with a decrease in both the rate of Ca$^{2+}$ mobilization and the amount of Ca$^{2+}$ mobilized (FIG. 3B). St6Gal-deficient B lymphocytes were next analyzed for their ability to accumulate phosphotyrosine on cellular proteins in response to anti-IgM stimulation. CD22 is among those proteins phosphorylated on tyrosine following B cell antigen-receptor activation, and this phosporylation is reported to recruit the SHP tyrosine phosphatase and other effector molecules to the antigen-receptor complex by SH2 binding interactions (Campbell & Klinman (1995) *Eur. J. Biochem.* 25: 1573–1579; Law et al. (1996) *J. Exp. Med.* 183: 547–560). Phosphotyrosine accumulation on CD22 was observed following anti-IgM stimulation of ST6Gal-deficient B cells however, reduced levels of cell surface CD22 (FIG. 2) necessitate additional quantitative studies on CD22 localization and relative phosphorylation potential. Nevertheless, among total cellular proteins analyzed following anti-IgM stimulation, a reduction in phosphotyrosine accumulation was noted on a protein migrating at approximately 42 kDa, with varied alterations on proteins of approximately 37 kDa (FIG. 3C).

The potential physiologic relevance of these alterations was addressed by analyzing the ability of ST6Gal-deficient mice to mount an immune response to T-independent and T-dependent antigens as judged by antibody production. Control and St6Gal-deficient mice were immunized with either DNP-Ficoll (T-independent antigen) or DNP conjugated to (KLH) (T-dependent antigen). Anti-DNP antibody titers were measured at various times after immunization. Mice deficient in Sia6LacNAc consistently failed to generate high titers of anti-DNP antibody following immunization with the T-independent antigen DNP-Ficoll (FIG. 4A). Control mice produced high anti-DNP IgM titers within 7–10 days of immunization, whereas mice lacking a functional ST6Gal allele were deficient in anti-DNP IgM and IgG$_1$ antibodies, and a reduced response was evident involving anti-DNP IgG$_3$ antibody production. In response to immunization with the T-dependent antigen DNP-KLH, ST6Gal-deficient mice were again severely impaired in their ability to generate an anti-DNP IgM antibody (FIG. 4B). Following a second "boost" immunization with DNP-KLH, Sia6LacNAc-deficient B cells still yielded reduced anti-DNP IgG$_1$ antibody levels and did not generate significant anti-DNP IgG$_3$ antibody. From these studies it is clear that mice deficient in the Sia6LacNAc trisaccharide are impaired in their ability to mount immune responses.

Discussion

The effector role of the ST6Gal sialyltransferase in B lymphocyte activation discloses an additional level of biologic control operating at the immune cell surface through oligosaccharide variation. Production of the Sia6LacNAc trisaccharide does not appear to be necessary for B lymphocyte development but is required for efficacious immune responses. Although B cells from ST6Gal-deficient mice display a significant reduction in CD22 cell surface levels, this is unlikely to account for the immune deficiencies observed because reduced CD22 expression in mice bearing a heterozygous CD22 null allele did not affect B cell immune function (O'Keefe et al. (1996) *Science* 274: 798–801; Otipoby et al. (1996) *Nature* 384: 634–637; Sato et al. (1996) *Immunity* 5: 551–562; Nitschke et al. (1997) *Curr. Biol.* 7: 133–143). Moreover, ST6Gal-deficient mice present a severe and widespread immunodeficiency much unlike that reported for CD22-deficient mice. Our results indicate that the function of ST6Gal encompasses distinct and unique activities in regulating immune responsiveness that may only partially overlap with the function of CD22.

B cell activation and acquisition of an anergic state reduces cell surface IgM levels, and activation is also reported to downregulate CD22 (Pezzutto et al. (1988) *J. Immunol.* 140: 1791–1795; Dorken et al. (988) *J. Immunol.* 136: 4470–4479). Sia6LacNAc-deficient B cells exhibit characteristics that may reflect prior aberrant antigen-receptor signal transduction leading to an anergic phenotype. Reduced IgM levels on ST6Gal-deficient B lymphocytes is similar to the anergic phenotype that develops following naive B cell stimulation by endogenous antigen production (Goodnow (1996) *Proc. Nat'l. Acad. Sci. USA* 93: 2264–2271). Nevertheless, Sia6LacNAc-deficient B cells do not exhibit an activated phenotype. Hypothesis as to how Sia6LacNAc may normally function in mature B lymphocytes requires knowledge of Sia6LacNAc expression.

A subset of secreted or cell surface lymphoid glycoproteins carries the Sia6LacNAc ligand of CD22. Some of these have been identified and include IgM, CD45, and CD22 itself (Stamenkovic et al. (1991) *Cell* 66: 1133–1144; Braesch-Anderson & Stamenkovic (1994) *J. Biol. Chem.* 269: 11783–11786; Hanasaki et al. (1995) *J. Biol. Chem.* 270: 7533–7542; Hickman et al. (1972)*J. Biol. Chem.* 247: 2156–2163; Sato et al. (1993) *Biochemistry* 32: 12694–12704). Although selective high-affinity binding of CD22 to soluble IgM has been reported (Hanasaki et al., supra.), the stoichiometry of cell surface CD22-IgM interaction is reported to be low both before and after B cell stimulation (Leprince et al. (1993) *Proc. Nat'l. Acad. Sci. USA* 90: 3236–3240; Hanasaki et al. (1995) *J. Biol. Chem.* 270: 7543–7550; Peaker et al. (1993) *Eur. J Biochem.* 23: 1358–1363). Because conditions employed in the latter type of experiment can dissociate lectin binding, homotypic and heterotypic cell interactions involving antigen receptors of B and T lymphocytes may normally occur by CD22-CD22 or CD22-CC45 Sia6LacNAc-dependent binding. Within B cells, loss of Sia6LacNAc on IgM and CD22 may thereby lead to aberrant antigen-receptor complex assembly at the cell surface. Perhaps Sia6LacNAc plays a role in the structural stabilization of one or more B lymphocyte membrane molecules that participate in antigen-receptor signal tranduction. The observed reductions in serum IgM and cell surface CD22 levels could reflect a destabilizing effect of Sia6LacNAc deficiency, including increased clearance of serum glycoproteins.

Altered protein phosphotyrosine accumulation following ST6Gal-deficient B cell activation nevertheless implies the dysfunction of signal transduction events emanating from the B cell antigen-receptor complex. The identification of altered phosphoproteins would further define the mechanisms by which ST6Gal acts in B cell activation. Such uncertainties are common and presently exist regarding the mechanism of CD22 function (Cyster and Goodnow (1977) *Immunity* 6: 509–517). It is of importance to understand how molecules that collaborate in signal transduction are able to associate with the B cell antigen-receptor complex in a normal membrane milieu without covalent binding interactions.

The position of oligosaccharides such as Sia6LacNAc at the extracellular side of the plasma membrane indicates that such molecules have evolved to function in cell-cell and receptor subunit interactions (Marth, J. D. (1994) *Glycoconjugate J.* 11: 3–8; Varki & Marth (1995) *Semin. Dev. Biol* 6: 127–138). Additionally, the functions of glycosyltransferases and glycosidases have been found in some cases to be focused on a particular cell lineage (Chui et al. (1997) *Cell* 90: 157–167). In these studies, we have observed the preferential accumulation of Sia6LacNAc on lymphoid cell surfaces among hematopoietic cell types. We have further observed what appears to be a cell-type specific role for ST6Gal and Sia6LacNAc in regulating B lymphocyte immune function. No evidence for T cell dysfunction using in vitro anti-CD3 activation methods has been found thus far. Further research in understanding the B lymphoid role of Sia6LacNAc should illuminate the reason for the more severe and widespread immune deficiency is observed in Sia6LacNAc-deficient mice than in studies of CD22-null mice. It is possible that the presence of CD22 in the absence of its ligand may be especially deleterious to B lymphocyte function by inappropriate localization and sequestration of intracellular signalling molecules. Alternatively, a redundancy in CD22 function mediated by other as yet unidentified Sia6LacNAc-binding lectins operating at the B lymphocyte cell surface that also play important roles in lymphocyte adhesion and intracellular signaling. This latter hypothesis reflects the biologic paradigm exemplified by the sialyl-Lewis X oligosaccharide and the E-, L, and P-selectins in the inflammatory response involving leukocyte intravasation (Butcher and Picker, *Science,* 272:60 (1996); Maly et al., *Cell,* 86:643 (1996); Frenette et al. (1996) *Cell* 84: 573–574)). While these possibilities can be tested, the immunodeficient phenotype of mice lacking Sia6LacNAc provides rationale for using Sia6LacNAc-dependent signal transduction in B cell activation and Sia6LacNAc expression to control immune dysfunction.

EXAMPLE 2

Figure 5:
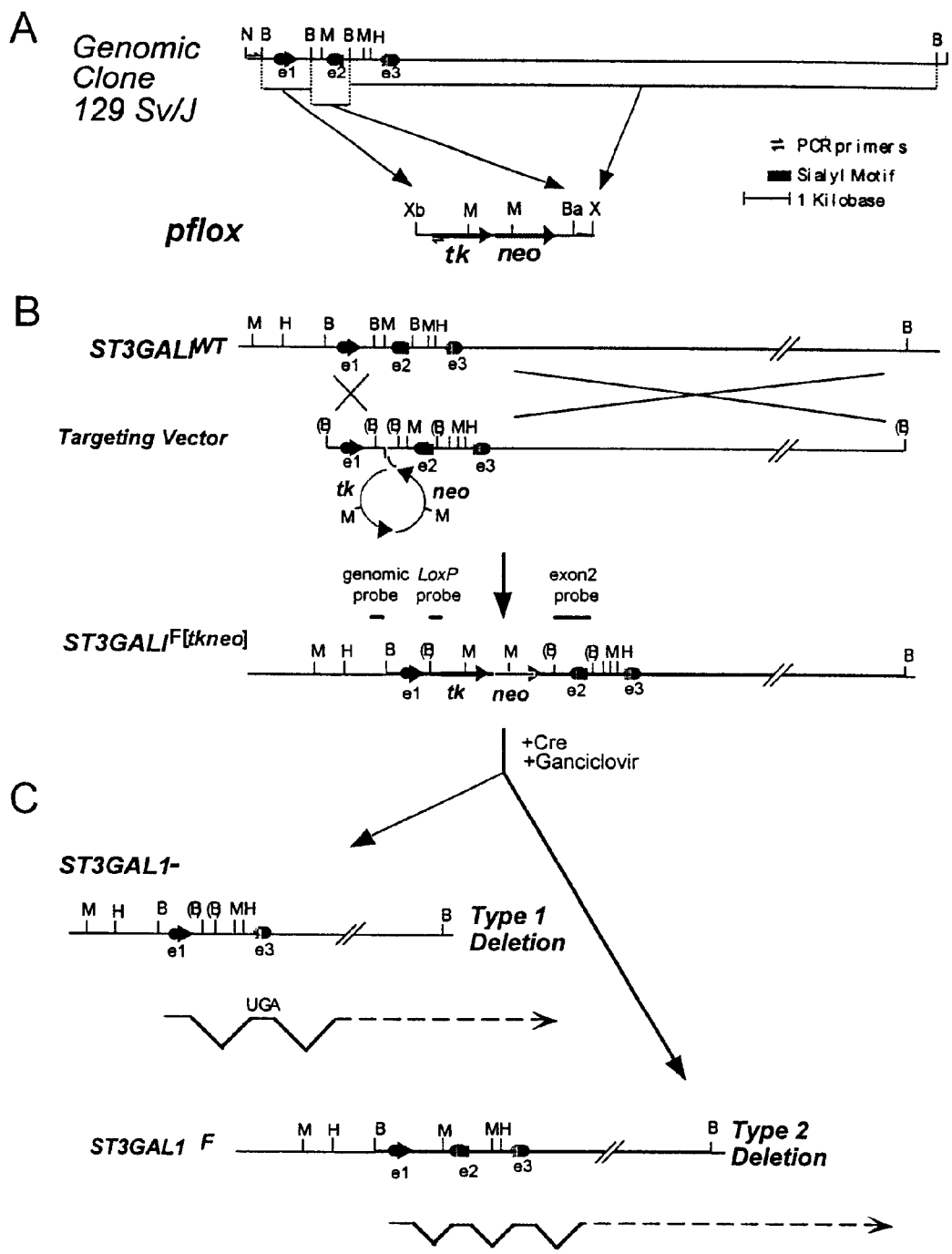
FIGS. 5A–5C is a schematic diagram of the ST3Gal I gene structure and the construction of ST3Gal I mutants.

Construction and Analysis of Transgenic Mice Deficient in Sialyltransferase ST3Gal Production of ST3Gal I deficient mice was accomplished similarly to production of ST6Gal deficiency in mice as described in Example 1. The essential difference was the location of the mutation (i.e., the ST3Gal I locus and not the ST6Gal locus). Mutation of the ST3Gal I allele involved deletion of an exon that is essential for ST3Gal I enzyme production (see FIG. 5). While any manner of insertional mutagenesis would also produce the same end result (i.e., ST3Gal I deficiency), we chose to mutate the gene by Cre recombination with deletion of exon 2. Placement of loxP sites in genomic context and surrounding exon 2 is shown in FIG. 5A. In FIG. 5B, the modified ST3Gal I allele is depicted as it occurred in embryonic stem cells following homologous recombination. Subsequently, (FIG. 5C) Cre recombination of ES cells heterozygous for the $F^{[tkneo]}$ allele, followed by ganciclovir selection, provided the type 1 and type 2 deletions. ES cells harboring the type 1 deletion were used to produce mice lacking ST3Gal I function.

Figure 6:
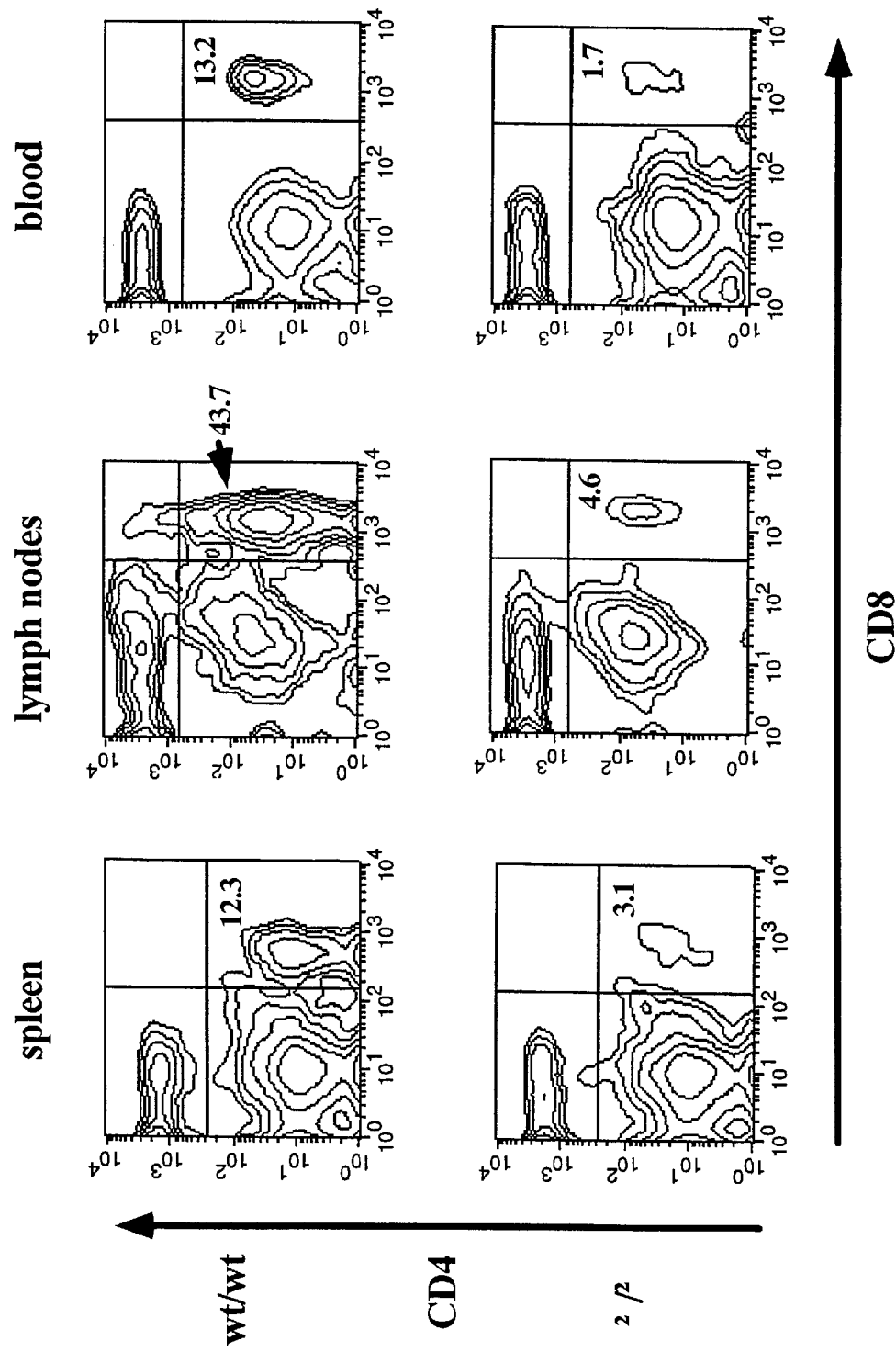
FIG. 6 shows the effect of loss of ST3Gal I activity on peripheral CD8$^+$ T cells. Samples obtained from spleen, lymph nodes, and blood from animals homozygous for wild-type ST3Gal I loci (top row) and from animals homozygous for an exon 2 deletion in the ST3Gal I locus were tested for the presence of CD4 and CD8. As shown in the figure, the numbers of CD8$^+$ T cells were dramatically reduced in samples obtained from animals having the ST3 Gal I deletion.

Mice lacking a wild-type ST3Gal I allele developed normally and appeared grossly unaltered in a pathogen-free environment. However, as a result of ST3Gal I deficiency, these mice had lost the vast majority of their mature $CD8^+$ T cells. These T cells were deficient from peripheral blood and were also greatly decreased in secondary lymphoid organs (see FIG. 6). The remaining $CD8^+$ T cells appeared inviable, as they were highly apoptotic when isolated. There was only a very minor decrease in the $CD4^+$ helper T cell lineage. These results demonstrate that deficiency of ST3Gal I dramatically decreases cytotoxic T cell abundance and function. Therefore, inhibition of the ST3Gal I would have a similar effect on CTL immune responses.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A method of inhibiting an immune response mediated by lymphocytes in a mammal, the method comprising administering to the mammal
   (a) a therapeutically effective amount of an agent that inhibits the activity of a sialytransferase involved in biosynthesis of a Siaα2-6Galβ1-4GlcNAc- moiety, thereby inhibiting a B lymphocyte-mediated response in the mammal; or
   (b) a therapeutically effective amount of an agent that inhibits the activity of a sialytransferase involved in biosynthesis of a Siaα2,3Galβ1-3GalNAc- moiety, thereby inhibiting a T lymphocyte-mediated response in the mammal.

2. The method according to claim 1, wherein the mammal is a human.

3. The method according to claim 1, wherein the immune response is a B lymphocyte-mediated immune response and the agent inhibits the activity of a sialytransferase involved in biosynthesis of the Siaα2-6Galβ1-4GlcNAc- moiety.

4. The method according to claim 3, wherein the sialyltransferase is ST6Gal sialyltransferase.

5. The method according to claim 1, wherein the immune response is a T lymphocyte-mediated immune response and the agent inhibits the activity of a sialytransferase involved in biosynthesis of the Siaα2,3Galβ1-3GalNAc- moiety.

6. The method according to claim 5, wherein the sialyltransferase is ST3Gal I sialyltransferase.

7. The method according to claim 5, wherein the T lymphocytes are $CD8^+$ T lymphocytes.

8. The method of claim 1, wherein the immune response is associated with graft rejection.

9. The method of claim 1, wherein the immune response is associated with an autoimmune disease.

10. The method of claim 1, wherein the immune response is associated with an allergy.

11. The method of claim 1, wherein the agent is a competitive inhibitor of the sialyltransferase.

12. The method of claim 1, wherein the agent resembles a substrate of the sialyltransferase.

13. The method of claim 12, wherein the substrate is a donor substrate.

14. The method of claim 13, wherein the donor substrate is CMP-sialic acid.

15. The method of claim 12, wherein the substrate is an acceptor substrate.

16. The method of claim 1, wherein the agent is a noncompetitive inhibitor of the sialyltransferase.

17. The method of claim 1, wherein the agent is an uncompetitive inhibitor of the sialyltransferase.

18. The method of claim 1, wherein the agent is a reversible inhibitor of the sialyltransferase.

19. The method of claim 1, wherein the agent is an irreversible inhibitor of the sialyltransferase.

* * * * *

UNITED STATES PATENT AND TRADEMARK OFFICE
CERTIFICATE OF CORRECTION

PATENT NO. : 6,376,475 B1 Page 1 of 1
DATED : April 23, 2002
INVENTOR(S) : Jamey D. Marth and James C. Paulson It is certified that error appears in the above-identified patent and that said Letters Patent is hereby corrected as shown below:

<u>Title page,</u>
Item [73], should read:
-- Abaron Biosciences, Inc. Del Mar, CA (US) and The Regents of the University of California, Oakland, CA (US) --

Signed and Sealed this

Twenty-seventh Day of May, 2003

JAMES E. ROGAN
*Director of the United States Patent and Trademark Office*